United States Patent
Axelsson et al.

(10) Patent No.: US 11,401,376 B2
(45) Date of Patent: Aug. 2, 2022

(54) CHEMICAL COMPOUNDS FOR COATING OF NANOSTRUCTURES

(71) Applicant: Spago Nanomedical AB, Lund (SE)

(72) Inventors: Oskar Axelsson, Höör (SE); Angelo Sanzone, Malmö (SE)

(73) Assignee: SPAGO NANOMEDICAL AB, Lund (SE)

( * ) Notice: Subject to any disclaimer, the term of this patent is extended or adjusted under 35 U.S.C. 154(b) by 576 days.

(21) Appl. No.: 16/477,995

(22) PCT Filed: Jan. 16, 2018

(86) PCT No.: PCT/EP2018/050975
§ 371 (c)(1),
(2) Date: Jul. 15, 2019

(87) PCT Pub. No.: WO2018/130713
PCT Pub. Date: Jul. 19, 2018

(65) Prior Publication Data
US 2019/0352459 A1 Nov. 21, 2019

(30) Foreign Application Priority Data
Jan. 16, 2017 (EP) ..................................... 17151653

(51) Int. Cl.
*C08G 65/336* (2006.01)
*C08K 5/5333* (2006.01)
(Continued)

(52) U.S. Cl.
CPC .......... *C08G 65/336* (2013.01); *C08K 5/5333* (2013.01); *B82Y 5/00* (2013.01); *B82Y 15/00* (2013.01)

(58) Field of Classification Search
CPC ............. C08G 65/336; Y10T 428/2995; C07F 7/1804; C08K 5/5333
(Continued)

(56) References Cited

U.S. PATENT DOCUMENTS 6,310,243 B1  10/2001  Almen et al.
9,150,686 B2 * 10/2015  Chun ................... C08G 59/306
(Continued)

FOREIGN PATENT DOCUMENTS

AU      2017276654 A1    1/2019
CN       101296927 A    10/2008
(Continued)

OTHER PUBLICATIONS

Belikov, V.G., "Pharmaceutical chemistry," MEDpress-inform, Moscow, 2007, pp. 27-29.
(Continued)

*Primary Examiner* — Margaret G Moore
(74) *Attorney, Agent, or Firm* — Harness Dickey & Pierce P.L.C.

(57) ABSTRACT

The present application relates to a chemical compound comprising an aromatic core, or a carbocyclic, non-aromatic, core, wherein the aromatic core is a benzene ring or a biphenyl; the carbocyclic, non-aromatic core is a 5 to 7 membered ring. The core has covalently attached thereto: at least two anchoring groups, each anchoring group comprising an activated silane group, wherein the anchoring groups have the following general formula -A-(CH$_2$)nSiY3 wherein A is a covalent bond or O, "n" is an integer from 1 to 3, and Y is independently a methoxy group or an ethoxy group; and at least one hydrophilic group extending from the core, the hydrophilic group comprising one or more hydrophilic polymer residues with a molecular composition of (aO+bN)/(cC+dS+eSi+fP)>0.3 where a, b, c, d, e and f are the mol (Continued)

percentage of oxygen (O), nitrogen (N), carbon (C), sulfur (S), silicon (Si) and phosphorus (P), respectively; wherein the hydrophilic polymer residue(s) is(are) selected, independently of each other if more than one hydrophilic group is present, from —(O—$CH_2$—$CH_2$)$_m$—OX, wherein X is $CH_3$ or H, and "m" is an integer from 6 to 25; and the number of hydrophilic groups extending from the core is from one to the number of ring structures in the core. The present invention also relates to compositions comprising the chemical compound and nanostructures comprising residues of the chemical compound as well as the use of such nanostructures. Furthermore, the invention relates to methods for obtaining the chemical compounds and the nanostructures.

16 Claims, 2 Drawing Sheets

(51) Int. Cl.
  *B82Y 5/00* (2011.01)
  *B82Y 15/00* (2011.01)
(58) Field of Classification Search
  USPC .......................................... 428/447; 556/445
  See application file for complete search history.

(56) References Cited

U.S. PATENT DOCUMENTS

| | | | | |
|---|---|---|---|---|
| 9,505,879 | B2* | 11/2016 | Harumashi | C08G 65/329 |
| 9,896,535 | B2* | 2/2018 | Chun | C08J 5/24 |
| 9,902,803 | B2* | 2/2018 | Chun | C07F 7/1876 |
| 10,597,412 | B2* | 3/2020 | Tak | C07D 303/12 |
| 2010/0098654 | A1 | 4/2010 | Pastorino et al. | |
| 2014/0179836 | A1* | 6/2014 | Chun | C07F 7/1876 528/33 |
| 2014/0350193 | A1 | 11/2014 | Axelsson et al. | |
| 2015/0105493 | A1* | 4/2015 | Chun | C08G 59/306 523/435 |
| 2015/0133622 | A1* | 5/2015 | Harumashi | C09J 143/04 568/616 |
| 2015/0148452 | A1* | 5/2015 | Chun | C08K 3/28 523/400 |
| 2016/0229948 | A1* | 8/2016 | Chun | C07F 7/1876 |

FOREIGN PATENT DOCUMENTS

| | | |
|---|---|---|
| CN | 101970541 A | 2/2011 |
| CN | 104530417 A | 4/2015 |
| RU | 0002473552 C2 | 1/2013 |
| RU | 2014111802 A | 10/2015 |
| WO | 2013041623 A1 | 3/2013 |
| WO | 2014057073 A1 | 4/2014 |
| WO | 2014057120 A1 | 4/2014 |
| WO | 2015144891 A1 | 10/2015 |
| WO | 2016050210 A1 | 4/2016 |

OTHER PUBLICATIONS

Bulte, J. W. M. and Modo, M. M. J. Eds. "Nanoparticles in Biomedical Imaging," Springer, 2008.
Zalipsky, S., et al., "Introduction to Chemistry and Biological Applications of Poly(ethylene glycol)," American Chemical Society, 1997.
European Medicines Agency, "Reflection paper on the data requirements for intravenous iron-based nano-colloidal products developed with reference to an innovator medicinal product," 2015.
Thomsen, H.S., et al., "Nephrogenic systemic fibrosis and gadolinium-based contrast media: updated ESUR Contrast Medium Safety Committee guidelines," European Society of Radiology, 2012.
Kanda, T., et al., "High Signal Intensity in Dentate Nucleus on Unenhanced T1-weighted MR Images: Association with Linear versus Macrocyclic Gadolinium Chelate Administration," Radiology, 2014.
Hermanson, G.T., "Bioconjugate Techniques," Elsevier, 2nd Edition, 2008.
Wuts, P.G.M., "Greene's Protective Groups in Organic Synthesis," John Wiley & Sons, Inc., Fifth Edition, 2014.
Ciardiello, J. J., et al., "An expedient strategy for the diversity-oriented synthesis of macrocyclic compounds with natural product-like characteristics," Tetrahedron, 72: 3567-3578 (2016).
Micovic, V.M., et al., "The Reduction of Acid Amides with Lithium Aluminum Hydride," J. Org. Chern., 1190-1200 (1953).
Bie, F., et al., "Synergistic Recognition of Halide Anions and Saccharides by Oligohydrazide Foldamers," European Journal of Organic Chemistry, 8135-8144 (2013).
Kissel, P., et al., "An Easy and Multigram-Scale Synthesis of Versatile AA- and AB-Type m-Terphenylenes as Building Blocks for Kinked Polyphenylenes," European Journal of Organic Chemistry, 2953-2955 (2009).
International Search Report from PCT Application No. PCT/EP2018/050975 dated Mar. 26, 2018.
Written Opinion from PCT Application No. PCT/EP2018/050975 dated Mar. 26, 2018.
Chavez et al., "Discrete, Hexagonal Boronate Ester-Linked Macrocycles Related to Two-Dimensional Covalent Organic Frameworks," Chemistry of Materials, 28: 4884-4888, Jun. 24, 2016.
Muraoka et al., "Reversible Ion Transportation Switch by a Ligand-Gated Synthetic Supramolecular Ion Channel," Journal of the American Chemical Society, 136: 15584-15595, Oct. 9, 2014.
Hawker et al., "Hyperbranched Poly(ethylene glycol)s: A New Class of Ion-Conducting Materials," Macromolecules, 29: 3831-3838, 1996.

* cited by examiner

CHEMICAL COMPOUNDS FOR COATING OF NANOSTRUCTURES

CROSS-REFERENCE TO RELATED APPLICATIONS

This patent application is national stage application under 35 U.S.C. § 371 of International Application No. PCT/EP2018/050975 filed on 16 Jan. 2018, which claims priority to European Application No. 17151653.7 filed on 16 Jan. 2017. The entire disclosures of each of the above recited applications are incorporated herein by reference.

TECHNICAL FIELD OF THE INVENTION

The present invention relates to polymeric coatings of nanomaterials, in particular chelating polymeric nanostructures incorporating paramagnetic manganese (II) ions, as well as methods to prepare said nanomaterials as well as use of the nanomaterials for visualizing or imaging biological material.

BACKGROUND

There are several medical applications of nanomaterials known in the art. Some of them, based on iron oxide, were in use as liver specific contrast agents but are no longer on the market because of low sales volumes. A huge literature regarding experimental use of those materials is available. (e. g. Bulte, J. W. M. and Modo, M. M. J. Eds. "Nanoparticles in Biomedical Imaging" Springer, 2008). The general approach to making nanomaterials biocompatible is to coat them with a flexible hydrophilic polymer. Poly ethylene glycol (PEG) is particularly effective at minimizing interaction with the immune system and proteins (see "Poly (ethylene glycol), Chemistry and Biological Applications", Eds. Harris and Zalipsky, 1997, ACS). Earlier it has been considered acceptable with some dissociation of coating residues from the nanomaterial in vivo but based on a reflection document from the European Medical Agency (EMA/CHMP/SWP/620008/2012) we anticipate that this will no longer be the case in the future.

Experiments (example 14, entry A) have shown that the m-PEG-silanes bound to polymeric nanostructures as described in WO 2013041623 A1 are prone to slow hydrolysis under neutral to basic conditions. This is a major drawback when considering these materials for use in medical products since it will impact the shelf-life of the product in a negative way.

An object of the present invention is to overcome these problems.

SUMMARY OF THE INVENTION

According to a first aspect of the invention, the above and other objects of the invention are achieved, in full or at least in part, by a chemical compound as defined by claim 1. According to this claim, the above object is achieved by a chemical compound comprising an aromatic core, or a carbocyclic, non-aromatic, core, wherein the aromatic core is a benzene ring or a biphenyl; the carbocyclic, non-aromatic core is a 5 to 7 membered ring; and the core having covalently attached thereto at least two anchoring groups each anchoring group comprising an activated silane group; wherein the anchoring groups have the following general formula -A-$(CH_2)_n SiY_3$ wherein A is a covalent bond or O, "n" is an integer from 1 to 3, and Y is independently a methoxy group or an ethoxy group; and at least one hydrophilic group extending from the core, the hydrophilic group comprising one or more hydrophilic polymer residues. The activated silane groups are able to covalently bind to the surface of a nanomaterial. The residues of the hydrophilic polymer have a molecular composition of $(aO+bN)/(cC+dS+eSi+fP)>0.3$ where a, b, c, d, e and f are the mol percentage of oxygen (O), nitrogen (N), carbon (C), sulfur (S), silicon (Si) and phosphorus (P), respectively wherein the hydrophilic polymer residue(s) is(are) selected, independently of each other if more than one hydrophilic group is present, from $-(O-CH_2-CH_2)_m-OX$, wherein X is $CH_3$ or H, and "m" is an integer from 6 to 25. Polymers having such a composition are regarded as hydrophilic. The number of hydrophilic polymer residues extending from the core is from one to the number of ring structures in the core. If more hydrophilic polymer residues extend from the core, the chemical compound is not useful for coating nanomaterials, since such compounds tend to form gels, which are not useful for the current application. If the core comprises more than one ring and more than one hydrophilic polymer residue, the hydrophilic residues may be attached to different rings.

The inventors have discovered that if the chemical compounds used for coating the nanostructures incorporate at least two silane groups having the ability to anchor the hydrophilic polymer to the surface of the nanomaterial, the product becomes stable under neutral conditions. Even if one of the silane groups detach from the surface of the nanomaterial, the polymer residue is still attached to the surface via the other silane group. The increased stability is a major advantage for the commercial value of the product and also makes the regulatory approval process easier.

One advantage over prior art of the chemical structures according to the present invention, is the ability to form a robust coating on a hydroxyl adorned nanomaterial, enabling a product for a commercially acceptable shelf life (>6 months) by engaging two separate functional groups for the purpose of binding, while still presenting a hydrophilic and bio-inert polymer towards the surroundings. This is especially important when the nanostructure is introduced into an organism, e.g. a human being, when used for medical purposes.

The chemical compound may comprise an aromatic core, wherein the aromatic core is a benzene ring or a biphenyl; the anchoring groups have the following general formula -A-$(CH_2)_n SiY_3$ wherein A is a covalent bond or O, "n" is an integer from 1 to 3, and Y is a methoxy group or an ethoxy group, wherein the at least two anchoring groups may be the same or different; and the hydrophilic polymer residue(s) is selected, independently of each other if more than one hydrophilic group is present, from $-(O-CH_2-CH_2)_m-OX$, wherein X is $CH_3$ or H, and "m" is an integer from 6 to 25. Such a compound is suitable to form a hydrolytically stable coating of a nanomaterial or nanostructure. In addition, such a compound has the advantage of being synthetically easily accessible.

The anchoring groups may be the same or different. The anchoring groups may differ with respect to "A", the integer "n" and/or to "Y". The three "Y"-groups in each anchoring group may be the same or different.

According to another embodiment, the chemical compound, wherein the aromatic core is a benzene ring, has the general formula 1, Formula 1

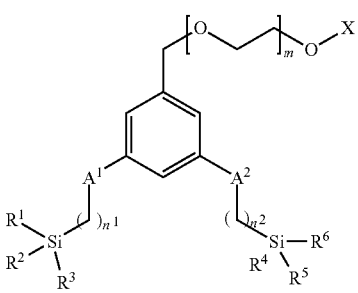

wherein $A^1$ and $A^2$ are independently selected from the group consisting of a covalent bond or O; "$n^1$" is an integer from 1 to 3; "$n^2$" is an integer from 1 to 3; $R^1$ to $R^6$ are independently selected from a methoxy group and an ethoxy group; "m" is an integer from 6 to 25; and X is methyl. Thus, in this embodiment, the three Y groups in one of the anchoring groups are denoted $R^1$, $R^2$ and $R^3$, and the three Y groups in a second anchoring group are denoted $R^4$, $R^4$ and $R^6$.

According to yet another embodiment, $A^1$ and $A^2$ are O, "$n^1$" is 3, "$n^2$" is 3, $R^1$ to $R^6$ are ethoxy, and X is methyl.

According to another embodiment, the chemical compound, wherein the aromatic core is a benzene ring, has the general formula 1, Formula 1

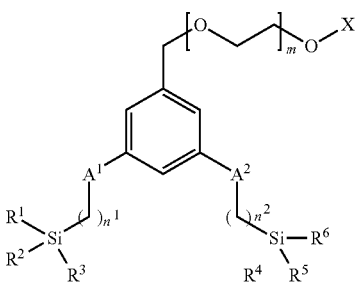

wherein $A^1$ and $A^2$ are O; "$n^1$" is 3; "$n^2$" is 3; $R^1$ to $R^6$ are independently selected from a methoxy group and an ethoxy group; "m" is an integer from 12 to 20; and X is methyl.

According to another embodiment, the chemical compound, wherein the aromatic core is a benzene ring, has the general formula 1, Formula 1

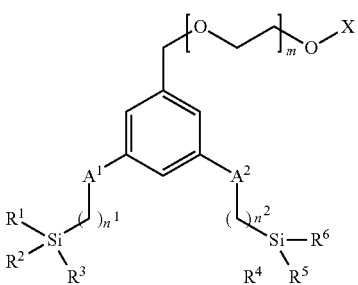

wherein $A^1$ and $A^2$ are a covalent bond; "$n^1$" is 2; "$n^2$" is 2; $R^1$ to $R^6$ are independently selected from a methoxy group and an ethoxy group; "m" is an integer from 12 to 20; and X is methyl.

The chemical compound may comprise a carbocyclic, non-aromatic core, wherein the carbocyclic, non-aromatic core is a 5 to 7 membered ring; the activated silane groups independently are -A-$(CH_2)_n SiY_3$ where A is covalent bond or O and "n" is an integer from 1 to 3 and Y is a methoxy group or an ethoxy group; and the hydrophilic polymer residue(s) is (independently are) —$(O-CH_2-CH_2)_m$—OX where X is $CH_3$ or H and "m" is an integer from 6 to 25. Such a compound gives a very stable coating of nanomaterials or nanostructures and is available from commercially available starting materials.

According to a second aspect of the invention, a composition comprising a chemical compound according to the invention and a carrier is provided. The carrier may be a solvent, such as dioxane or an alcohol such as ethyleneglycol.

According to one embodiment, the composition comprises at least two different chemical compounds according to the invention. The different chemical compounds may vary with respect to the core, such that certain compounds have an aromatic core and other compounds in the composition have a carbocyclic, non-aromatic, core. The different chemical compounds may also, or alternatively, vary with respect to the length of the polymer chain, i.e. the integer "m" may vary. Other features that may vary are A, X, Y and R as well as the integers "$n^1$" and "$n^2$". The composition comprising a mixture of the chemical compounds may have the advantage of being cheaper to produce.

According to another embodiment, the composition comprises compounds wherein $A^1$ and $A^2$ are O, "$n^1$" is 3, "$n^2$" is 3, $R^1$ to $R^6$ are ethoxy, and X is methyl.

According to a third aspect of the invention, a coated nanostructure comprising residues of the chemical compounds according to the invention or of a chemical compound comprising an aromatic core, or a carbocyclic, non-aromatic, core, and; the core having covalently attached thereto: at least two anchoring groups, each anchoring group comprising an activated silane group; and at least one hydrophilic group extending from the core, the hydrophilic group comprising one or more hydrophilic polymer residues with a molecular composition of (aO+bN)/(cC+dS+eSi+fP)>0.3 where a, b, c, d, e and f are the mol percentage of oxygen (O), nitrogen (N), carbon (C), sulfur (S), silicon (Si) and phosphorus (P), respectively; wherein the number of hydrophilic groups extending from the core is from one to the number of ring structures in the core; is provided, wherein one or both of the activated silanes in each of the chemical compounds, has been covalently bonded to the surface of the nanostructure core. Such a nanostructure has, when loaded with a magnetic ion such as manganese(II) or gadolinium(III), the properties of high relaxivity and low toxicity, which is especially advantageous, since it has the properties compatible with a tumor selective MRI contrast agent.

Thus, a coated nanostructure comprising residues of the chemical compounds according to the invention is provided, wherein one or both of the activated silanes in each of the chemical compounds, has been covalently bonded to the surface of the nanostructure core. Such a nanostructure has, when loaded with a magnetic ion such as manganese(II) or gadolinium(III), the properties of high relaxivity and low toxicity, which is especially advantageous, since it has the properties compatible with a tumor selective MRI contrast agent.

Thus, a coated nanostructure comprising residues of a chemical compound comprising an aromatic core, or a carbocyclic, non-aromatic, core, and; the core having covalently attached thereto: at least two anchoring groups, each anchoring group comprising an activated silane group; and at least one hydrophilic group extending from the core, the hydrophilic group comprising one or more hydrophilic polymer residues with a molecular composition of (aO+bN)/(cC+dS+eSi+fP)>0.3 where a, b, c, d, e and f are the mol percentage of oxygen (O), nitrogen (N), carbon (C), sulfur (S), silicon (Si) and phosphorus (P), respectively; wherein the number of hydrophilic groups extending from the core is from one to the number of ring structures in the core; is provided, wherein one or both of the activated silanes in each of the chemical compounds, has been covalently bonded to the surface of the nanostructure core. Such a nanostructure has, when loaded with a magnetic ion such as manganese(II) or gadolinium(III), the properties of high relaxivity and low toxicity, which is especially advantageous, since it has the properties compatible with a tumor selective MRI contrast agent.

The nanostructures are coated in order to reduce their interactions with e.g. proteins and/or calcium ions in a biological environment and also their interactions with each other. The amount of coating is thus important. When compounds having longer hydrophilic polymer residues are used to coat the nanostructures, a smaller amount of the chemical compound(s) according to the invention is needed in order to reduce the above-mentioned interactions. Thus the overall density of (O—$CH_2$—$CH_2$) is important.

According to one embodiment, the coated nanostructure comprises a polymeric framework comprising, or adorned with, at least five geminal bisphosphonate groups having the general formula —P=O($OR^{11}$)($OR^{12}$), wherein $R^{11}$ and $R^{12}$ are independently selected from a negative charge, H, an alkyl group and an aryl group, wherein the polymeric framework further comprises monomer residues containing a geminal bisphosphonate group and two organo-oxysilane groups. Such nanostructures have the advantage of being able to chelate to di- or trivalent cations strongly, thus having the potential to form the base of a contrast agent or imaging agent.

According to another embodiment, the coated nanostructure has a hydrodynamic diameter of 4 to 8 nm. The hydrodynamic diameter is determined by DLS. One advantage of such coated nanostructures is that the nanostructures can be eliminated from the body of an organism via the kidneys.

Important advantages of the coated nanostructures according to the present invention over prior art are the combination of a good product stability with a relaxivity significantly higher than the materials currently on the market, combined with a size suitable for selective accumulation in tumor tissue and a good biotolerability. This renders the nanostructures of the current invention suitable for use as a contrast agent for e.g. MRI (magnetic resonance imaging), PET (positron emission tomography) and/or SPECT (single-photon emission computed tomography), and in particular for tumor imaging. When functioning as a contrast agent, the nanostructure comprises an paramagenetic ion (for MRI imaging) or a radioactive isotope (for PET and/or SPECT imaging) chelated to the polymeric framework. A particular advantage of the coated nanostructrues according to the invention is that the coating can prevent calcium ion induced aggregation when the polymeric framework of the nanostructure is chelating to di- or trivalent cations (example 14, coating precursor 6 (of example 1)). Another advantage of the coated nanostructures according to the present invention is that they are resistant to the rather vigorous process conditions which are necessary to achieve optimal chelating ability (Example 14, coating precursor 6 (of example 1)) shows a good result; Example 18 shows a bad result from a compound being outside the scope of the current invention).

According to yet another embodiment, the coated nanostructure further comprises a paramagnetic ion. The paramagnetic ion may be manganese or gadolinium. Such coated nanostructures may be used as MRI contrast agents.

According to yet another embodiment, the coated nanostructure further comprises a manganese(II) or gadolinium (III) ion. Such coated nanostructures may be used as MRI contrast agents. Advantages of using these coated nanostructures as MRI contrast agents compared to conventional contrast agents are their very high relaxivity and low toxicity.

Furthermore, the use of manganese instead of gadolinium as the paramagnetic component circumvents the toxicity issues (Thomsen, H. S., Morcos, S. K., Almén, T. et al. Eur Radiol (2013) 23: 307. doi:10.1007/s00330-012-2597-9 "Nephrogenic systemic fibrosis and gadolinium-based contrast media: updated ESUR Contrast Medium Safety Comittee guidelines") and current concerns (Kanda, T. et al. Radiology 2014; 270:834-841 "High Signal Intensity in the Dentate Nucleus and Globus Pallidus on Unenhanced T1-weighted MR Images: Relationship with Increasing Cumulative Dose of a Gadolinium based Contrast Material") connected with gadolinium. Coated nanostructures comprising paramagnetic magnesium ions are preferably used in humans, since such nanostructures have a lower toxicity than nanostructures comprising gadolinium ions. However, since coated nanostructures comprising paramagnetic gadolinium ions have a higher signal strength, thus giving images of higher resolution, such nanostructures may be used for research purposes or for veterinary purposes.

The use of abundant manganese instead of the relatively rare gadolinium also has cost advantages in the production of the material.

When the coated nanostructure comprises bisphosphonate groups, the paramagnetic ion is presumably chelated to the phosphonate groups.

According to one embodiment, the coated nanostructure further comprises a radionuclide for imaging and/or radiotherapy. Such coated nanostructures may be used as a PET and/or SPECT contrast agent. Advantages of using these coated nanostructures as a PET and/or SPECT contrast agent compared to conventional contrast agents are that they locate to tumors via the Enhanced-Permeation-Retention mechanism.

According to fourth aspect of the invention, a coated nanostructure further comprising a paramagnetic manganese or a paramagnetic gadolinium ion or a composition comprising the coated nanostructure further comprising a manganese(II) or a gadolinium(III) ion, for use as an MRI contrast agent is provided.

According to another aspect of the invention, a coated nanostructure further comprising a radionuclide for imaging and/or radiotherapy or a composition comprising the coated nanostructure further comprising a radionuclide for imaging, for use in PET and/or SPECT imaging or in radiotherapy is provided.

According to one aspect of the invention, a composition comprising coated nanostructures according to the invention and a carrier is provided. The carrier may be a solvent, such as a polar solvent. Especially, the solvent may be water. The composition may be administered by a parenteral route, such as intravenously or intra-arterial. In certain instances, the composition is administered orally.

According to another aspect of the invention, a method for obtaining the chemical compounds according to the invention is provided. The method comprises hydrosilylation of two terminal double bonds as the last chemical step. This has the advantage that the most sensitive group is introduced as the last step.

According to another aspect of the invention, a method for obtaining the coated nanostructure according to the invention is provided. The method comprises the steps of providing a nanostructure core of a polymeric framework comprising geminal bisphosphonate groups; and contacting said nanostructure core with at least one of the chemical compounds according to the invention in a solvent, preferably an aqueous solvent.

According to one embodiment, the method is performed in the presence of urea at a concentration of 0.1-1 M. This has the advantage that the yield of the coated nanostructures is substantially increased.

According to another aspect of the invention, a nanostructure obtainable by the method according to the invention is provided.

Definitions of Terms

The term "activated silane" as used herein refers to a silane of the following type $RSi(Y)_3$, where Y independently is/are an alkoxy group, aryloxy group, a halogen, a dialkylamino group, a nitrogen-containing heterocycle or an acyloxy group.

The term "hydrophilic polymer residue" as used herein refers to an organic residue that promotes solubility in aqueous solvents and in the current invention it is implicit that they are bio-inert, which excludes polypeptides and complex carbohydrates. Examples of suitable hydrophilic organic residues are any groups containing carbon with a molecular composition $(aO+bN)/(cC+dS+eSi+fP)>0.3$ where a, b, c, d, e and f are the mol percentage of oxygen (O), nitrogen (N), carbon (C), sulfur (S), silicon (Si) and phosphorus (P), respectively. The hydrophilic polymer residues referred to are often residues of hydrophilic polymers attached to nanomaterials.

The term "residue" is used to describe the moiety of a larger molecule that stems, i.e., is the residue of a precursor molecule, in the same sense that proteins are said to be composed of amino acid residues since the covalent bonds between them transforms the amino and acid functionalities to amides. Typically, a polymer chain is said to be made up from monomer residues and a polymer covalently linked to a surface is said to be a polymer residue.

The term "hydrophilic polymer" as used herein refers to a non-attached polymer that will promote solubility in aqueous solvents when attached to a nanostructure and in the current invention it is implicit that such a polymer is bio-inert, which excludes polypeptides and complex carbohydrates. Examples of suitable hydrophilic polymers are polymers composed of any group containing carbon atoms and with a molecular composition $(aO+bN)/(cC+dS+eSi+fP)>0.3$ where a, b, c, d, e and f are the mol percentage of oxygen (O), nitrogen (N), carbon (C), sulfur (S), silicon (Si) and phosphorus (P), respectively.

The term "nanomaterial" as used herein relates to an entity with at least one dimension smaller than 100 nm, e.g. particles, spheres, shells, flakes, rods, strings, tubes and ribbons.

The term "nanostructure" as used herein relates to an entity with a total diameter from 1-100 nm of essentially globular shape, i.e. excluding shells, flakes, rods, strings, tubes and ribbons.

The term "globular" as used herein is meant to describe nanostructures with a shape such that the minor axis is no less than half of the major axis, i.e. the longest axis through the center (point of weight) of the structure is no more than twice the length of the shortest axis through the same point.

The term "polymeric framework" as used herein relates to a covalently bound group of atoms forming either a multi-branched, tree-like structure, or a network structure with multiple crosslinks. This constitutes the skeleton or scaffolding of the nanostructure. The skilled person realizes that the random nature of the polymerization process causes the material to be a mixture of many similar but not identical, branching patterns, crosslink positions and molecular weights.

"m-PEG" refers to structures $CH_3-(OCH_2CH_2)_n-OH$ where n depends on the circumstances. The term m-PEG$_{x-y}$ refers to a material containing a mixture of different chain lengths where the main components of the mixture has n=x-y where x and y are integers and y>x. Typical values in the current invention are n=6-9 or n=12-20. When a chemical name of a compound carrying a polydisperse m-PEG substituent is given in the current text we have chosen to use the name ω-methyl-(ethyleneoxy)$_{x-y}$ for said substituent, where w indicates that the methyl group is located at the end of the structure and x and y are as above.

The term "geminal bisphosphonate group" refers to two phosphonate groups separated by one carbon atom, i.e. the phosphonate groups are bound to the same carbon. Compounds comprising such a geminal bisphosphonate group are often referred to as 1,1-bisphosphonates (or 1,1-diphosphonates). The phosphonate groups in the geminal bisphosphonate group may be substituted. In some embodiments the phosphonate groups each have the formula $-P=O (OR^1)(OR^2)$ wherein $R^1$ and $R^2$ are independently selected from the group consisting of a negative charge, H, alkyl and aryl.

The term "bio-inert" as used herein refers to a material that is bio-compatible, i.e. harmless to a living organism and at the same time is essentially stable to degradation in-vivo.

The term "DLS" as used herein is an acronym for dynamic light scattering, a particle sizing method, and may also be referred to as Photon Correlation Spectroscopy or Quasi-Elastic Light Scattering. The DLS sizes given as stated in the text and in the claims, if nothing else is specified, refer to the position of the maximum of the volume average peak for a sample measured at 25° C. in neutral aqueous solution with an ionic strength corresponding to 150 mM NaCl. The hydrodynamic diameter is the diameter of the equivalent hard sphere as calculated from the diffusion coefficient, according to the Stokes-Einsteins equation. The diffusion coefficient is in turn calculated from the time dependent light scattering data obtained by DLS technique. Depending on whether the number average, volume average, or scattered intensity average is used, the values may be somewhat different. The volume average is generally the most useful, since it shows which particle size the bulk of the material has. The average diameters referred to in this text refer to volume averages.

The terms "hydrocarbon" and "hydrocarbon chain" are used herein to denote an organic residue consisting of hydrogen and carbon. The hydrocarbon may be fully saturated or it may comprise one or more unsaturations. The hydrocarbon may contain any number of carbon atoms between 1 and 50.

The term "alkyl" as used herein refers to a straight or branched hydrocarbon chain fully saturated (no double or triple bonds). The alkyl group may in the present text have 1 to 15 carbon atoms. The alkyl group of the compounds may be designated as "$C_{1-15}$ alkyl" or similar designations. Typical alkyl groups include, but are in no way limited to, methyl, ethyl, propyl, isopropyl, butyl, isobutyl, tertiary butyl, pentyl, hexyl and the like.

The term "lower alkyl" as used herein refers to an alkyl having 1-8 carbon atoms.

Whenever it is used herein, unless otherwise stated, a numerical range such as "1 to 8" or "1-8" refers to each integer in the given range; e.g. "1 to 8 carbon atoms" means that the alkyl group may consist of 1 carbon atom, 2 carbon atoms, 3 carbon atoms, etc., up to and including 8 carbon atoms. There are, however some exceptions which are clear to the skilled persons. In particular, whenever a range is given herein for a molar ratio, such as the P/N molar ratio or the Si/P molar ratio in the nanostructures, for a diameter or size, for a pH, for a period of time, for a concentration, for an osmolality or for a temperature, the range includes also all decimal numbers falling within the range.

As used herein, the term "alkoxy" refers to the formula —OR wherein R is a C1-8 alkyl, e.g. methoxy, ethoxy, n-propoxy, 1-methylethoxy (isopropoxy), n-butoxy, iso-butoxy, sec-butoxy, tert-butoxy, amyloxy, iso-amyloxy and the like. An alkoxy may be optionally substituted.

As used herein the term "aryloxy" refers to RO— in which R is an aryl, wherein "aryl" refers to a carbocyclic (all carbon) ring or two or more fused rings (rings that share two adjacent carbon atoms) that have a fully delocalized pi-electron system. The aryl ring may be a 4-20 membered ring. Examples of aryl groups include, but are not limited to, benzene, naphthalene, anthracene, phenanthrene and azulene. An aryl group may be optionally substituted, e.g., phenoxy, naphthalenyloxy, azulenyloxy, anthracenyloxy, naphthalenylthio, phenylthio and the like. An aryloxy may be optionally substituted.

As used herein the term "acyl" refers to a carbonyl group attached to an alkyl or aryl group, i.e. —C(=O)—R, where R is alkyl or aryl.

As used herein the term "acyloxy" refers to an oxygen atom connected via an acyl group, i.e. RC(=O)—O—, with R defined as above.

As used herein the term "heterocycle" refers to a stable 3 to 18 membered ring structure which consists of carbon atoms and from one to five heteroatoms selected from the group consisting of nitrogen, oxygen and sulfur. The heterocycle may be monocyclic, bicyclic or tricyclic.

The term "strong base" as used herein refers in the current context to bases that are stronger than hydroxide and not compatible with aqueous environments.

The term "hydrodynamic diameter" as used herein refers to the diameter of the hypothetical hard sphere that diffuses at the same speed as the particle. Hydration and shape is included in the behavior of the sphere. The term is also known as "Stokes diameter" or "Stokes-Einstein diameter".

The term "conjugate" as used herein refers to a molecular entity that is a fluorescence marker, dye, spin-label, radioactive marker, ligand to a biological receptor, chelate, a peptide, enzyme inhibitor, enzyme substrate, antibody or antibody related structure. See e.g. "Bioconjugate Techniques", Greg T. Hermanson second edition, Elsevier 2008, ISBN 978-0-12-370501-3 for background on the subject.

The terms "handle for conjugation" and "attachment point" both refer to a bifunctional molecule that can bind to, or be incorporated in, the polymer network but leaving one reactive group that can be linked to a conjugate, as defined above. A typical, but not exclusive, example is $(EtO)_3SiCH_2CH_2CH_2NH_2$.

The term "coating" is used to describe a layer of molecules covalently attached to a surface or outer layer of a nanomaterial or a nanostructure. In this context it excludes physisorbed or non-covalently bound polymers.

The terms "coated nanomaterial" or "coated nanostructure" describe nanomaterials with a coating as defined above. To describe the part of a coated nanomaterial or a coated nanostructure that is not part of the coating we use the term nanomaterial core or nanostructure core. These latter terms are also used to describe nanomaterials or nanostructures that have no coating.

The term "coating density" is used to describe how closely the coating molecules are packed on the surface of a nanomaterial or a nanostructure. The unit preferred herein is molecules/nm$^2$ but in the literature, the unit µmol/m$^2$ is also common. The numerical values can be converted by multiplying the value in molecules/nm$^2$ by 1.6.

The term "surface" of nanostructures is less obvious than for macroscopic objects and is in this context used to describe those outer parts of a nanomaterial or a nanostructure that are accessible to chemical modification with polymers.

The acronym "Ms" stands for mesylate.

The term "radionuclide" refers to an unstable form of a chemical element that decays radioactively, resulting in the emission of α, β and/or γ radiation.

As used herein, the expression "radionuclide for imaging and/or radiotherapy" refers to actinium-225 ($^{225}$Ac); copper-62 ($^{62}$Cu); copper-64 ($^{64}$Cu); copper-67 ($^{67}$Cu); gallium-67 ($^{67}$Ga); gallium-68 ($^{68}$Ga); holmium-166 ($^{166}$Ho), indium-111 ($^{111}$In); lead-212 ($^{212}$Pb), lutetium-177 ($^{177}$Lu); radium-223 ($^{223}$Ra); rhenium-186 ($^{186}$Re); rhenium-188 ($^{188}$Re); rubidium-82 ($^{82}$Rb); samarium-153 ($^{153}$Sm); strontium-89 ($^{89}$Sr); technetium-99m ($^{99m}$Tc$^{3+}$); thallium-201 ($^{201}$Tl); thorium-227 ($^{227}$Th); yttrium-86 ($^{86}$Y); yttrium-90 ($^{90}$Y); and zirconium-89 ($^{89}$Zr). The expression "a radionuclide for imaging and/or radiotherapy" also encompasses combinations of two or more of the above-mentioned radionuclides.

As used herein, the expression "radionuclide for imaging" refers to copper-62 ($^{62}$Cu); copper-67 ($^{67}$Cu); gallium-67 ($^{67}$Ga); gallium-68 ($^{68}$Ga); indium-111 ($^{111}$In); lutetium-177 ($^{177}$Lu); rhenium-186 ($^{186}$Re); rubidium-82 ($^{82}$Rb): technetium-99m ($^{99m}$Tc$^{3+}$); Thallium-201 ($^{201}$Tl); yttrium-86 ($^{86}$Y) and zirconium-89 ($^{89}$Zr). The expression "a radionuclide for imaging" also encompasses combinations of two or more of the above-mentioned radionuclides.

As used herein, the expression "radionuclide for PET imaging" refers to copper-62 ($^{62}$Cu); gallium-68 ($^{68}$Ga); rubidium-82 ($^{82}$Rb); yttrium-86 ($^{86}$Y) and zirconium-89 ($^{89}$Zr). The expression "a radionuclide for PET imaging" also encompasses combinations of two or more of the above-mentioned radionuclides.

As used herein, the expression "radionuclide for SPECT imaging" refers to gallium-67 ($^{67}$Ga); indium-111 ($^{111}$In), technetium-99m ($^{99m}$Tc$^{3+}$) and thallium-201 ($^{201}$Tl). The expression "a radionuclide for SPECT imaging" also encompasses combinations of two or more of the above-mentioned radionuclides.

As used herein, the expression "radionuclide for radiotherapy" refers to actinium-225 ($^{225}$Ac); copper-64 ($^{64}$Cu); copper-67 ($^{67}$Cu); holmium-166 ($^{166}$Ho); lead-212 ($^{212}$Pb);

lutetium-177 ($^{177}$Lu); radium-223 ($^{223}$Ra); rhenium-186 ($^{186}$Re); rhenium-188 ($^{188}$Re); samarium-153 ($^{153}$Sm); strontium-89 ($^{89}$Sr); thorium-227 ($^{227}$Th) and yttrium-90 ($^{90}$Y). The expression "a radionuclide for radiotherapy" also encompasses combinations of two or more of the above-mentioned radionuclides.

As used herein, the expression "radionuclide for PET imaging and radiotherapy" refers to actinium-225 ($^{225}$Ac); copper-62 ($^{62}$Cu); copper-64 ($^{64}$Cu); copper-67 ($^{67}$Cu); gallium-68 ($^{68}$Ga); holmium-166 ($^{166}$Ho); lead-212 ($^{212}$Pb); lutetium-177 ($^{177}$Lu); radium-223 ($^{223}$Ra); rhenium-186 ($^{186}$Re); rhenium-188 ($^{188}$Re); rubidium-82 ($^{82}$Rb); samarium-153 ($^{153}$Sm); strontium-89 ($^{89}$Sr); thorium-227 ($^{227}$Th); yttrium-90 ($^{90}$Y) and zirconium-89 ($^{89}$Zr). The expression "a radionuclide for PET imaging and radiotherapy" also encompasses combinations of two or more of the above-mentioned radionuclides.

As used herein, the expression "radionuclide for SPECT imaging and radiotherapy" refers to actinium-225 ($^{225}$Ac); copper-64 ($^{64}$Cu); copper-67 ($^{67}$Cu); gallium-67 ($^{67}$Ga); holmium-166 ($^{166}$Ho); indium-111 ($^{111}$In); lead-212 ($^{212}$Pb); lutetium-177 ($^{177}$Lu); radium-223 ($^{223}$Ra); rhenium-186 ($^{186}$Re), rhenium-188 ($^{188}$Re); samarium-153 ($^{153}$Sm); strontium-89 ($^{89}$Sr); technetium-99m ($^{99m}$Tc$^{3+}$); thallium-201 ($^{201}$Tl); thorium-227 ($^{227}$Th) and yttrium-90 ($^{90}$Y). The expression "a radionuclide for SPECT imaging and radiotherapy" also encompasses combinations of two or more of the above-mentioned radionuclides.

ICP-OES means Ion Coupled Plasma-Optical Emission Spectroscopy, an elemental analysis method.

ICP means ICP-OES in this context.

DETAILED DESCRIPTION

Figure 1:
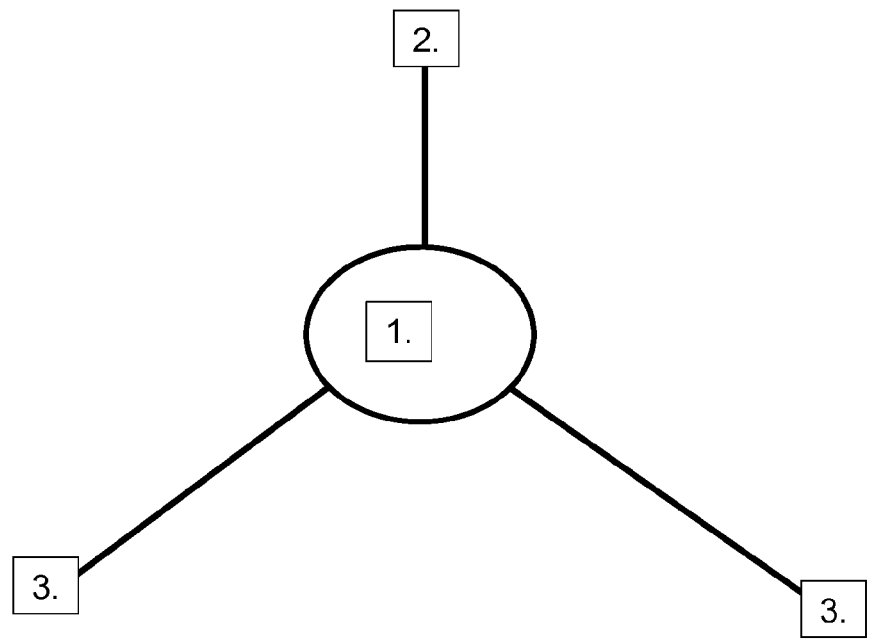
FIG. 1 is a schematic representation of a chemical compound according to the present invention, wherein 1 represents a core, 2 represents a hydrophilic polymer residue and 3 represents an activated silane.

The present disclosure relates to chemical compounds comprising a core structure carrying at least three substituent groups, two of which comprise an activated silane group (3) and one or more comprise a hydrophilic polymer residue or residues (2) (see FIG. 1). The hydrophilic polymer residue (2) is in many cases a mixture of different chain lengths so the specific chemical compound is usually found in a mixture of chemical compounds that are identical in their core parts and activated silane parts but different in the number of monomer residues making up the polymer part. Using the mixture has the advantage of being substantially cheaper than materials with a specific number of monomer residues making up the polymer part.

It is of course also conceivable to have more than two groups of activated silane (3) to anchor the compounds to the surface as shown in example 14, see coating precursor 41, but this proved less attractive because of the poor solubility of the coated nanostrucures. Some non-limiting examples of the hydrophilic polymer residues (2) of FIG. 1 are polyethylene glycol (also called PEG, polyethylene oxide (PEO), or (polyoxyethylene (POE)), m-PEG (methoxypolyethylene glycol), polyvinyl pyrrolidinione, acrylates and methacrylates with various polar sidechains, poly(glycidyl methyl ether) or poly(glycidylalcohol).

Some non-limiting examples of the core (1) in FIG. 1 are aromatic hydrocarbons such as benzene, or naphthalene, or biphenyl; or linked aromatic hydrocarbons such as diphenyl ether or, diphenyl methane; or fused ring systems such as anthraquinone; or heterocyclic compounds such as pyridine, or pyridazine, or pyrimidine, or pyrazine, or pyrrole, or imidazole, or benzimidazole, piperidine, pyrrolidine, or carbocyclic compounds such as cyclopentane, cyclohexane, and cycloheptane. They can be introduced in various ways, some of which are shown in scheme 1a. Some, like the linked ring structures biphenyl, diphenyl ether, diphenyl methane or anthraquinone, allow more than one, such as two, polymer residues to be introduced. One skilled in the art can envision several more core structures like larger aliphatic rings, polycyclic aliphatic ring systems or large polycyclic aromatic or complicated heterocyclic systems.

In some embodiments the core is a carbocyclic, non-aromatic 5-7 membered ring; and/or the hydrophilic polymer residue(s) is (independently are) —(O—CH$_2$—CH$_2$)$_m$—OX where X is CH$_3$ or H and "m" is an integer from 6 to 25; and/or the activated silane is -A-(CH$_2$)$_n$Si(OY)$_3$ where A is an oxygen or a covalent bond and "n" is an integer from 1 to 3 and Y is methyl or ethyl.

We have found that compounds where the core is one ring having two activated silanes and two hydrophilic polymers are not useful for coating nanomaterials but rather form gels. Thus, structures with more than one polymer chain per ring structure of the core are excluded from the current invention (See example 14, Coating precursor 20). The number of hydrophilic polymer residues extending from the core should preferably be from one to the number of ring structures in the core. In example 14, coating precursor 14 is shown as an example with two rings in the core and two hydrophilic polymer residues.

In some embodiments the core is aromatic, such as a benzene ring or a biphenyl; and/or the hydrophilic polymer residue(s) is (independently are) —(O—CH$_2$—CH$_2$)$_m$—OX where X is CH$_3$ or H and m=6-25; and/or the activated silane is -A-(CH$_2$)$_n$Si(OY)$_3$ where A is an oxygen or a covalent bond and n is an integer from 1 to 3 and Y is methyl or ethyl.

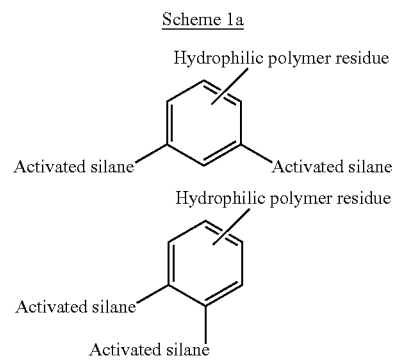

Scheme 1a

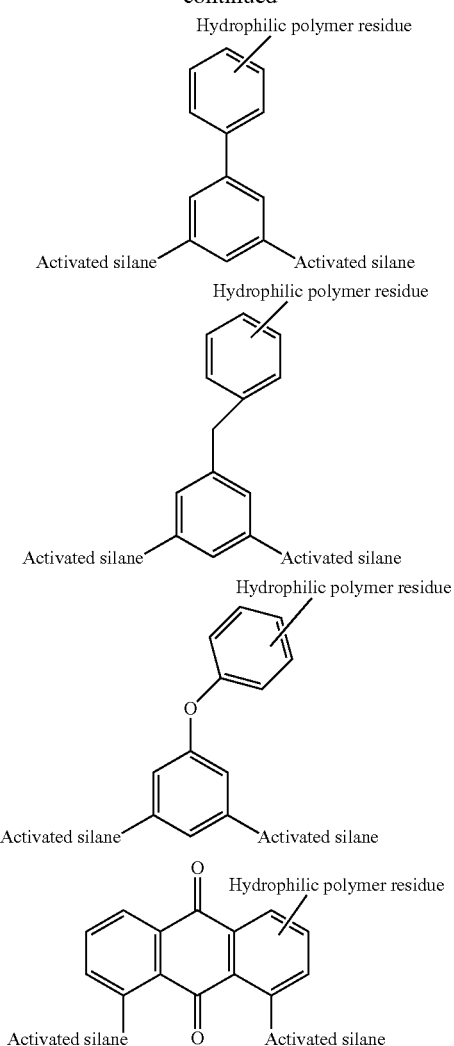
Scheme 1b
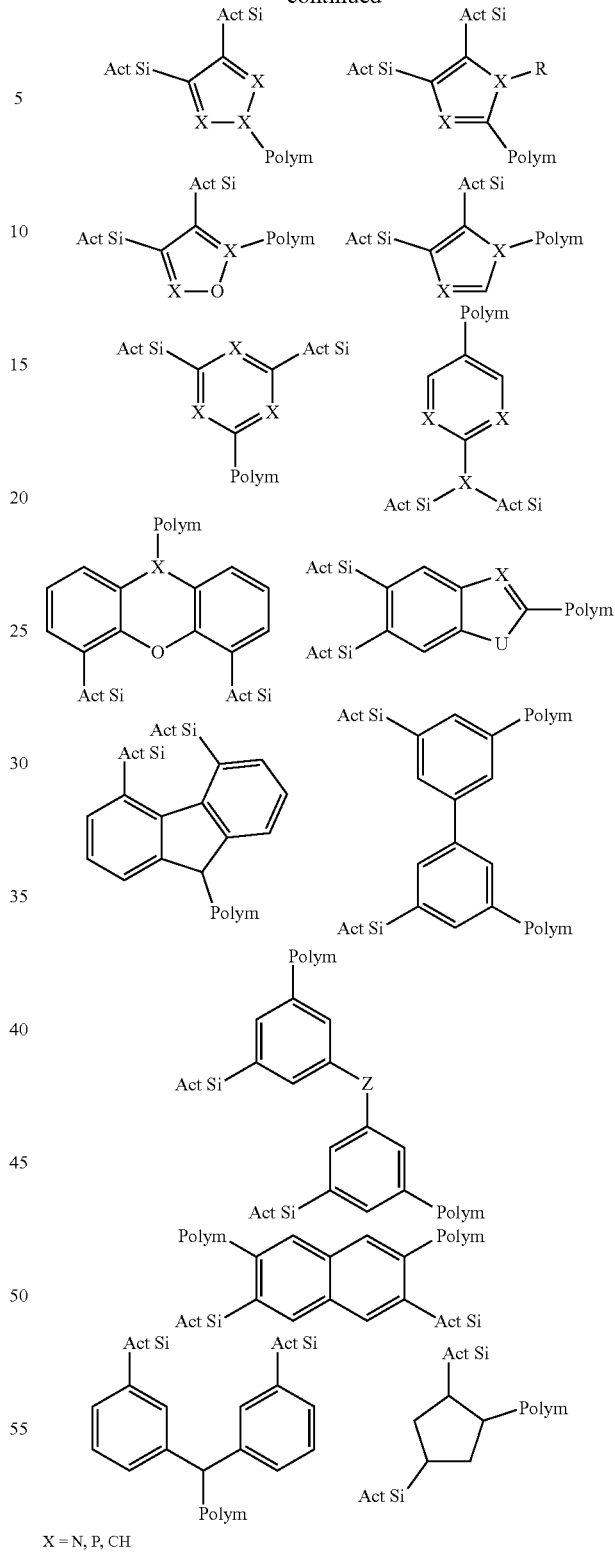
X = N, P, CH
U = CH₂, NH, S, O
Z = (CH₂)₂U, CH₂UCH₂
The hydrophilic polymer residue can be connected to the core in several ways, obvious to one skilled in the art, but bonds that are resistant to hydrolysis, in particular acid catalyzed hydrolysis, are advantageous as shown by the difference in stability of the nanostructures coated with the coating precursor 54 (see examples 11b and 18) and the coating precursor 6 (see examples 14, Coating precursor 6). The former, outside the scope of the current invention, is degraded substantially under the coating conditions whereas the latter, within the scope of the current invention, is robust. Some non-limiting examples of such bonds resistant to hydrolysis are ether bonds or carbon-carbon bonds as outlined in scheme 1c, where the benzene ring is to be construed as a generic core.

Scheme 1c

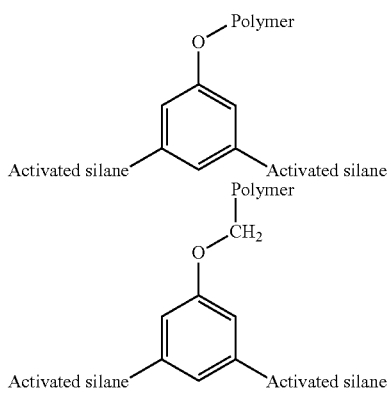

-continued

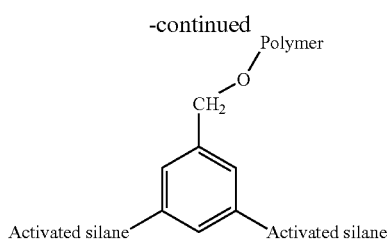

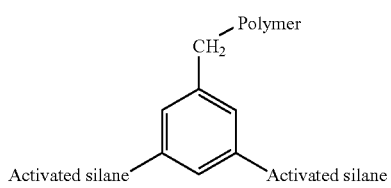

The chemical structures of the current invention can be synthesized from commercially available compounds. In the following is outlined some non-limiting examples of synthetic strategies that are suitable for accessing some of the compounds of schemes 2-15. As recognized by one skilled in the art, there are many alternative routes to reach the same target compounds. Thus, these methods are only to be seen as a sample of conceivable methods.

Scheme 2

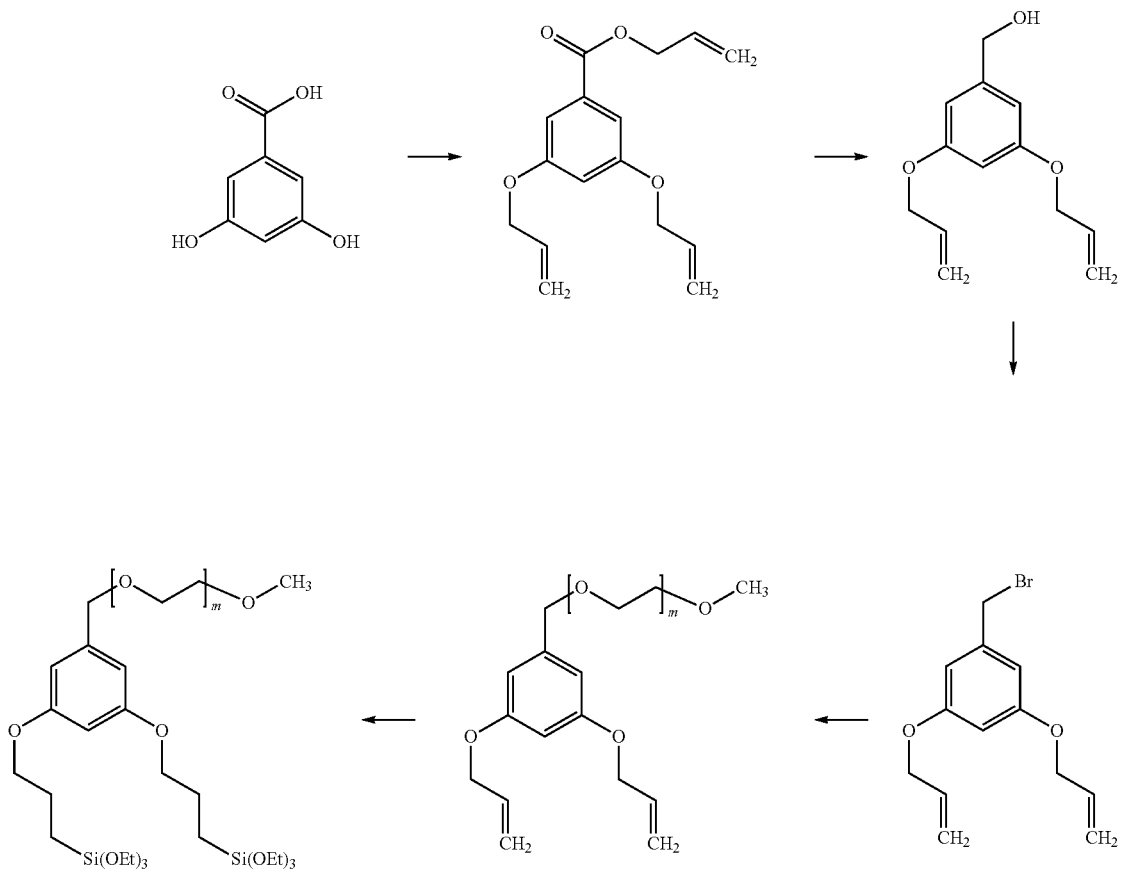

As shown in Scheme 2 and example 1, triple allylation of 3,5-dihydroxybenzoic acid followed by LAH (lithium aluminium hydride) reduction were adapted from the literature (Example 78 of Almén et. al. U.S. Pat. No. 6,310,243) and bromination was achieved by reaction of the resulting alcohol with PBr₃. Substitution of the bromine with the anion of m-PEG$_{12-20}$-OH was followed by hydrosilylation with HSi(OEt)₃ catalyzed by Karstedt's catalyst.

Scheme 3

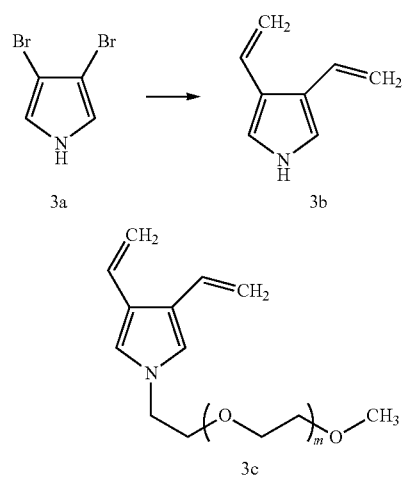

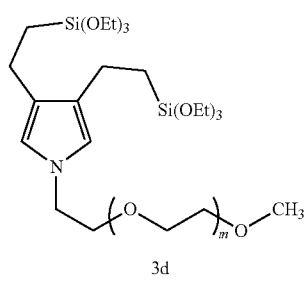

As shown in Scheme 3 compound 3d can be synthesized by a vinylation of 3,4-dibromo pyrrole (3a) via a cross-coupling reaction, such as a Stille coupling, followed by deprotonation of the nitrogen with a strong base, such as NaH, and the resulting anion can be coupled with a hydrophilic polymer carrying a suitable leaving group such as m-PEG$_{12-20}$-OMs (56). Finally, the two vinyl groups can be hydrosilylated with a silane such as (EtO)₃SiH and a catalyst, such as a platinum compound, such as Karstedt's catalyst.

Scheme 4

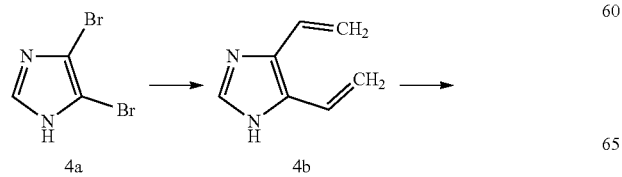

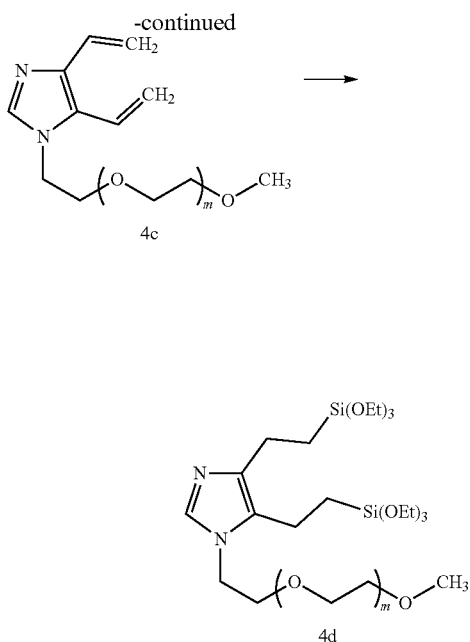

Compound 4d can be synthesized by vinylation of 4,5-dibromo imidazole (4a) via a cross-coupling reaction, such as a Stille coupling, followed by deprotonation of the nitrogen with a strong base, such as NaH, and the resultant anion can be coupled with a hydrophilic polymer carrying a suitable leaving group such as m-PEG$_{12-20}$-OMs (56). Finally, the two vinyl groups can be hydrosilylated with a silane such as (EtO)₃SiH and a catalyst, such as a platinum compound, such as Karstedt's catalyst.

Scheme 5

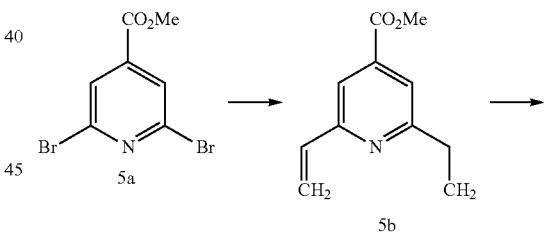

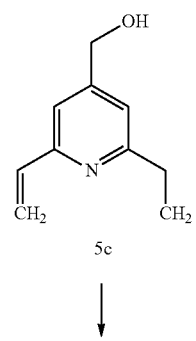

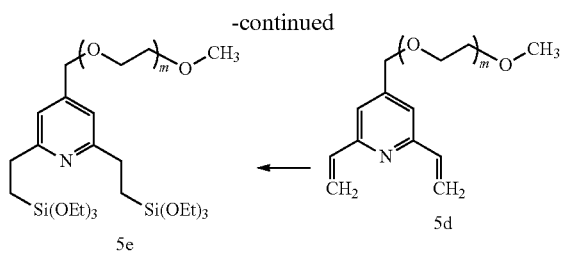

Compound 5e can be synthesized by vinylation of methyl 2,6-dibromoisonicotinate (5a) via a cross-coupling reaction, such as a Stille coupling, followed by selective reduction of the ester with a suitable hydride source. The resulting alcohol can be deprotonated with a strong base, such as NaH, and the resulting anion can be coupled with a hydrophilic polymer carrying a suitable leaving group such as m-PEG$_{12-20}$-OMs (56). Finally, the two vinyl groups can be hydrosilylated with a silane such as (EtO)$_3$SiH and a catalyst, such as a platinum compound, such as Karstedt's catalyst.

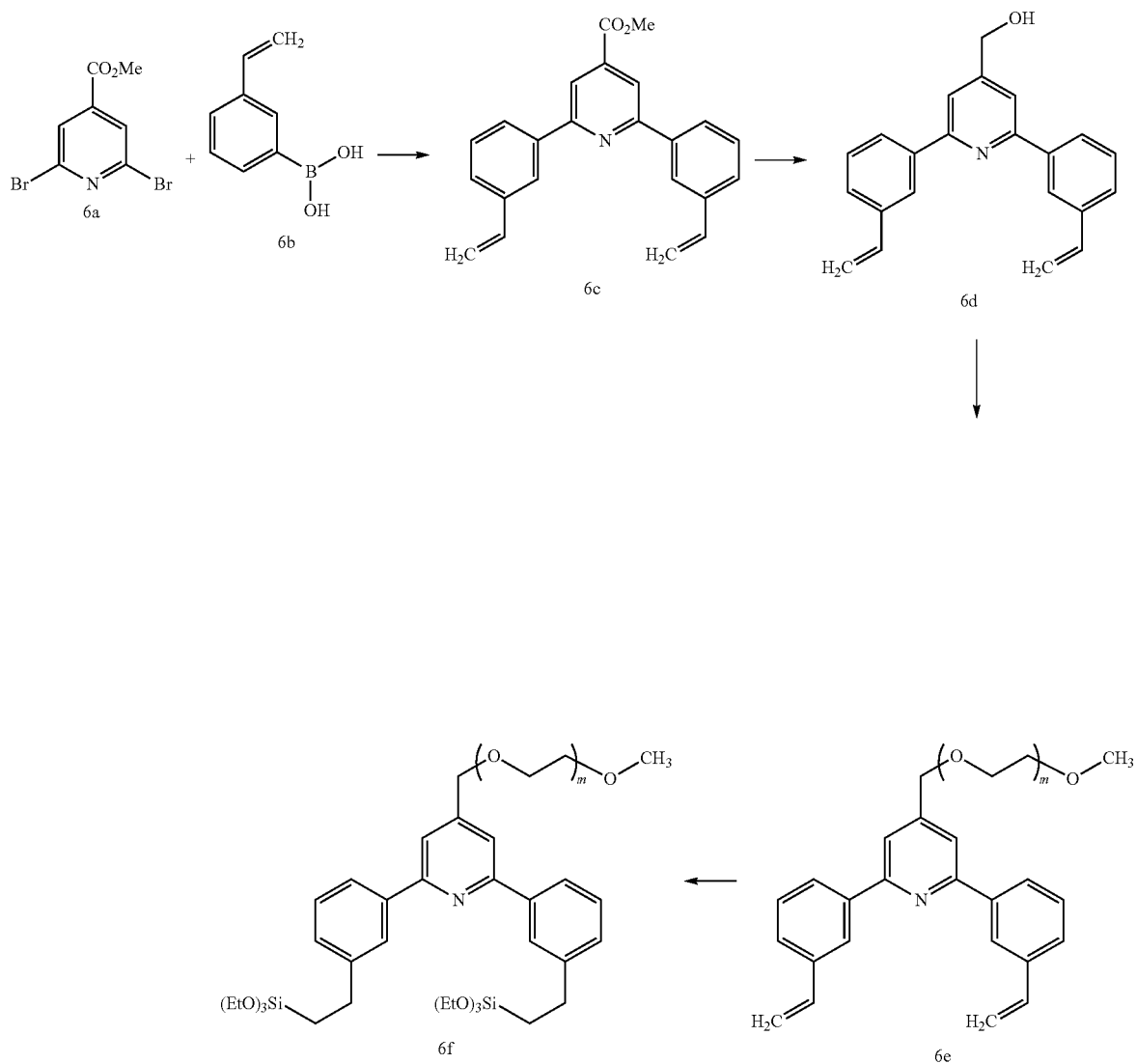

Scheme 6

Compound 6f can be synthesized via a cross-coupling reaction, such as a Suzuki coupling, between methyl 2,6-dibromoisonicotinate (6a) and 3-vinylphenylboronic acid (6b) followed by a selective reduction of the ester by a suitable hydride source. The resulting alcohol can be deprotonated with a strong base, such as NaH, and then coupled with a hydrophilic polymer carrying a suitable leaving group such as m-PEG$_{12-20}$-OMs (56). Finally, the two vinyl groups can be hydrosilylated with a silane such as (EtO)$_3$SiH and a catalyst, such as a platinum compound, such as Karstedt's catalyst.

Scheme 7

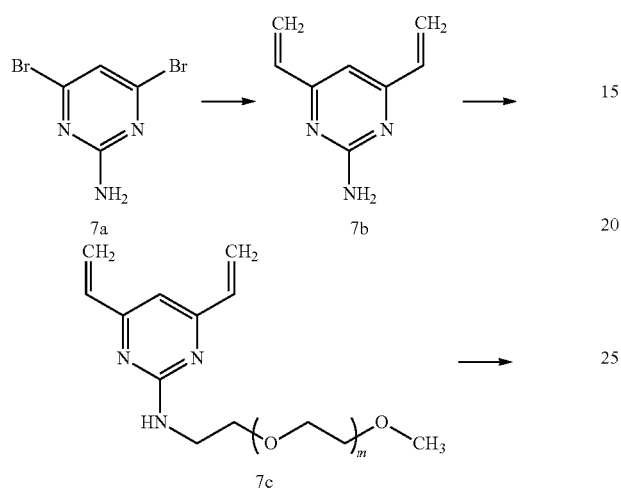

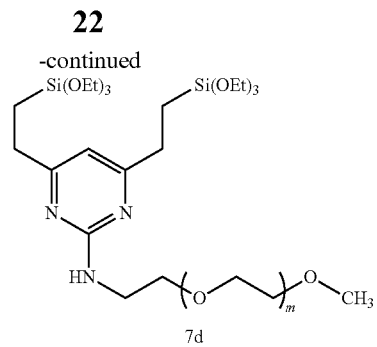

Compound 7c can be synthesized by vinylation of 2-amino-4,6-dibromopyrimidine (7a) via a cross-coupling reaction, e.g. Stille coupling, followed by PEGylation with an m-PEG carrying a suitable leaving group at one end, such as m-PEG$_{12-20}$-OMs (56). Finally, the two vinyl groups can be hydrosilylated with a silane such as (EtO)$_3$SiH and a catalyst, such as a platinum compound, such as Karstedt's catalyst.

Scheme 8

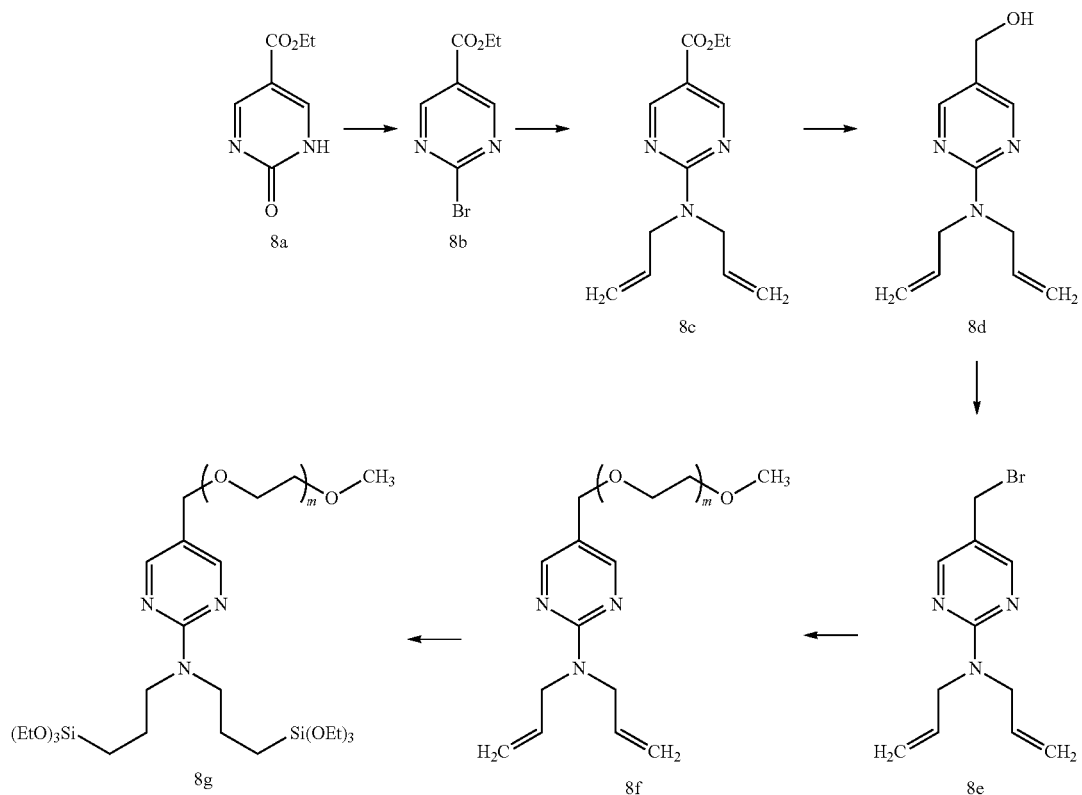

Compound 8b can be synthesized from ethyl 2-oxo-1,2-dihydropyrimidine-5-carboxylate (8a) by a halogenation, with a halogenation reagent such as POCl$_3$ or POBr$_3$, followed by nucleophilic substitution of the halogen with diallylamine. The ester can be selectively reduced by a suitable hydride source and the resulting alcohol 8d transformed to a leaving group such as a halogen with a suitable reagent such as a halogenation reagent, e.g. as PBr$_3$. A hydrophilic polymer with a suitable functionality, such as an alcohol, at one end, such as m-PEG$_{12-20}$-OH, can be deprotonated by a strong base, such as NaH, and can then give a nucleophilic substitution at the benzylic position. Finally the two vinyl groups can be hydrosilylated with a silane such as (EtO)$_3$SiH and a catalyst, such as a platinum compound such as Karstedt's catalyst.

ring followed by halogenation at C2 using a halogenation reagent such as HBr and Br$_2$. The so installed halogen can be substituted by a hydrophilic polymer carrying a suitable functionality such as an amine, in particular a primary amine. An example of such a compound is m-PEG$_{12-20}$-NH$_2$ (2-(ω-methyl-ethyleneoxy$_{12-20}$)eth-1-ylamine). The remaining two aromatic bromides can undergo vinylation via a cross coupling reaction, such as the Stille reaction, to obtain a divinyl compound 9c that can be hydrosilylated with a silane such as (EtO)$_3$SiH and a catalyst, such as a platinum compound such as Karstedt's catalyst.

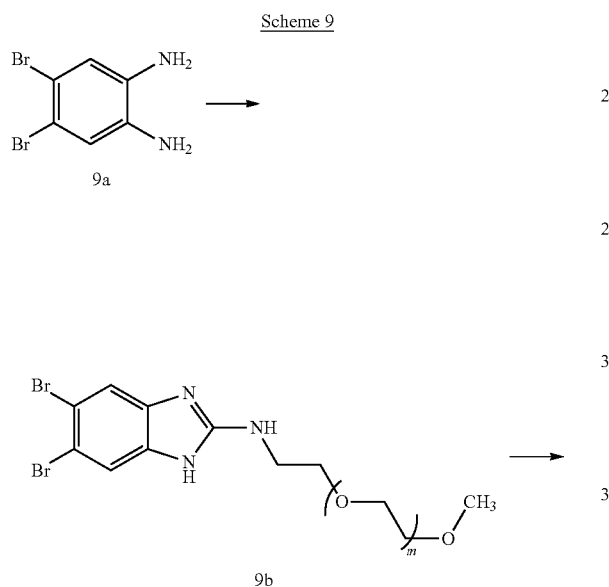

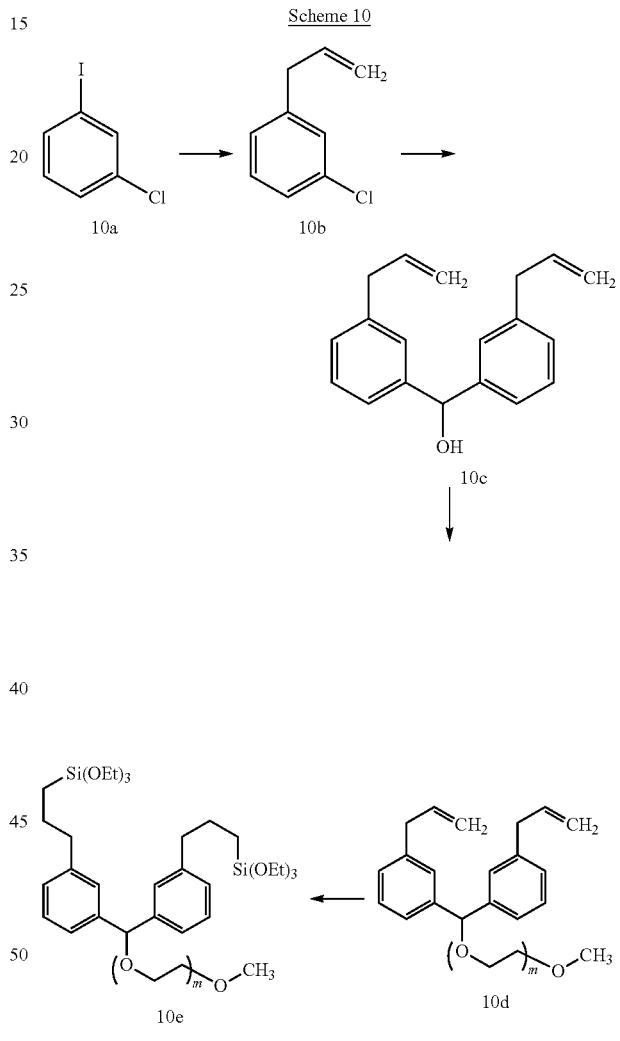

Compound 9b can be synthesized from 4,5-dibromo-1,2-diaminobenzene (9a), first by formation of the imidazole Compound 10b can be synthesized starting by allylation of methyl 3-chloroiodobenzene via a cross-coupling reaction, e.g. Stille coupling. The chloride of 10b can be exchanged with a metal, e.g. Mg, and then the organometallic species can react with ethyl formate to give the benzyl alcohol 10c, which can be deprotonated by a strong base, e.g. NaH, and then coupled with a hydrophilic polymer carrying a suitable leaving group such as m-PEG$_{12-20}$-OMs (56). Finally, the two double bonds of 10d could be hydrosilylated with a silane such as (EtO)$_3$SiH and a catalyst, such as a platinum compound such as Karstedt's catalyst.

Scheme 11

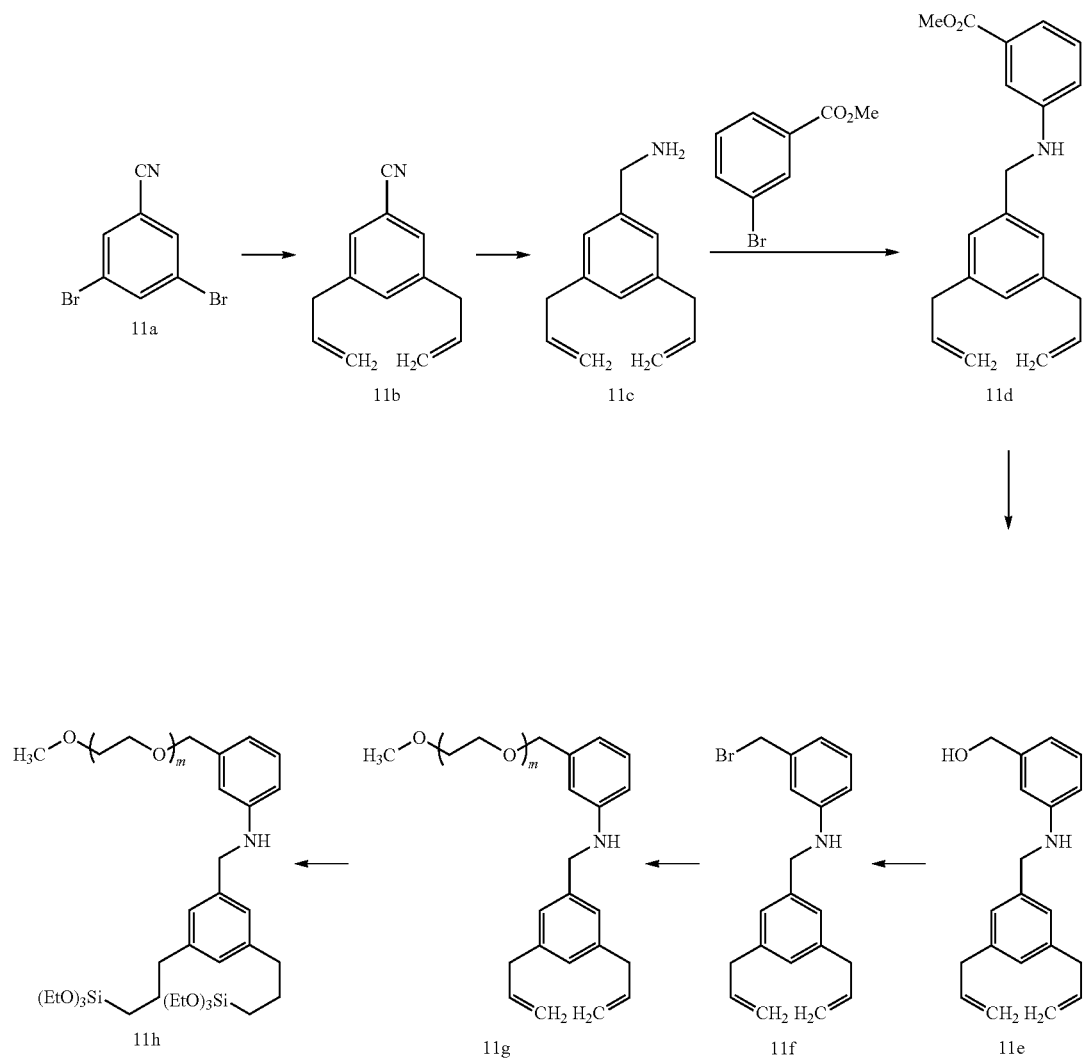

Compound 11h can be synthesized starting by allylation of 3,5-dibromobenzonitrile (11a) via a cross-coupling reaction, such as a Stille coupling. The cyano group can be selectively reduced by a suitable hydride source. The resulting amine 11c can be coupled with methyl 3-bromobenzoate, by a cross coupling reaction such as a metal catalyzed cross-coupling such as a copper-catalyzed reaction or a palladium-based reaction such as a Buchwald cross-coupling, followed by reduction of the ester by a suitable hydride source. The resulting alcohol 11e can then be converted to a leaving group, e.g. as a halogen such as bromide with a suitable reagent such as a halogenation reagent, e.g. as a bromination reagent such as $PBr_3$. A hydrophilic polymer with a suitable functionality, such as an alcohol, at one end, such as m-$PEG_{12-20}$-OH, can be deprotonated by a strong base, such as NaH, and can then give a nucleophilic substitution at the benzylic position forming 11g. Finally the two vinyl groups can be hydrosilylated with a silane such as $(EtO)_3SiH$ and a catalyst, such as a platinum compound, such as Karstedt's catalyst.

Scheme 12

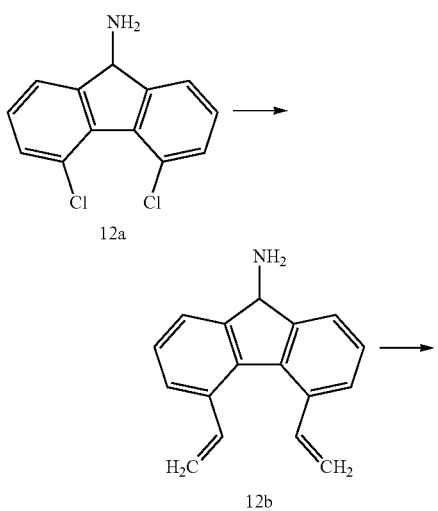

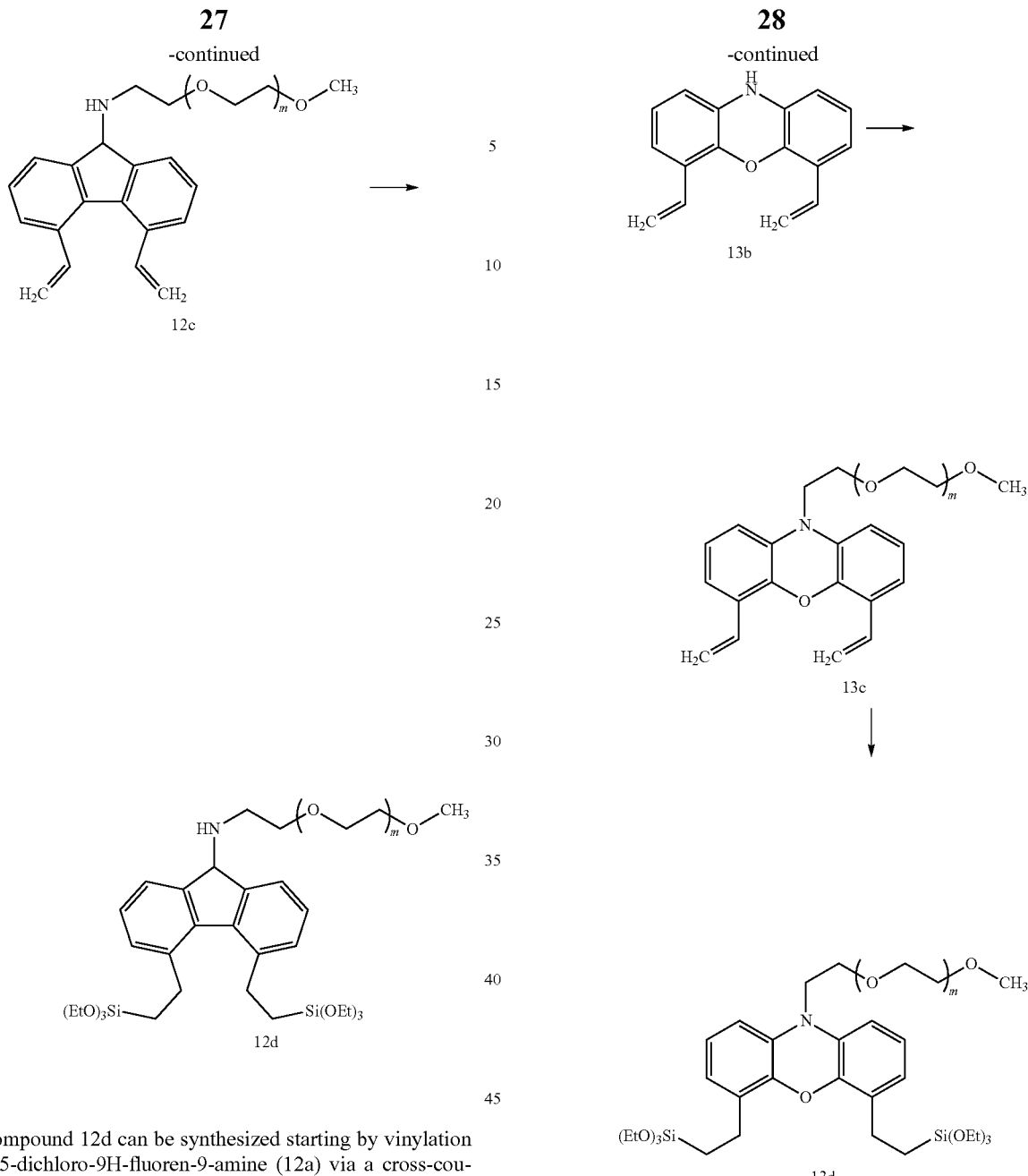

Compound 12d can be synthesized starting by vinylation of 4,5-dichloro-9H-fluoren-9-amine (12a) via a cross-coupling reaction, e.g. Stille or Suzuki reaction, followed by coupling with a hydrophilic polymer carrying a suitable leaving group such as mPEG$_{12-20}$-OMs (56). Finally, the two double bonds can be hydrosilylated with a silane such as (EtO)$_3$SiH and a catalyst, such as a platinum compound, such as Karstedt's catalyst to yield 12d.

Scheme 13

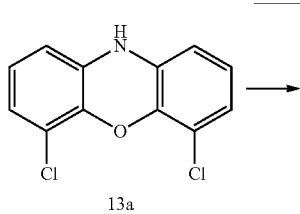

Compound 13d can be synthesized starting by allylation of 4,6-dichlorophenoxazine (13a) via a cross-coupling reaction, e.g. Stille reaction, followed by PEGylation with an with a m-PEG carrying a suitable leaving group at one end, such as m-PEG$_{12-20}$-OMs (56). Finally the two vinyl groups of 13c can be hydrosilylated, with e.g. (EtO)$_3$SiH and a catalyst, such as a platinum catalyst, such as Karstedt's catalyst to yield 13d.

Scheme 14
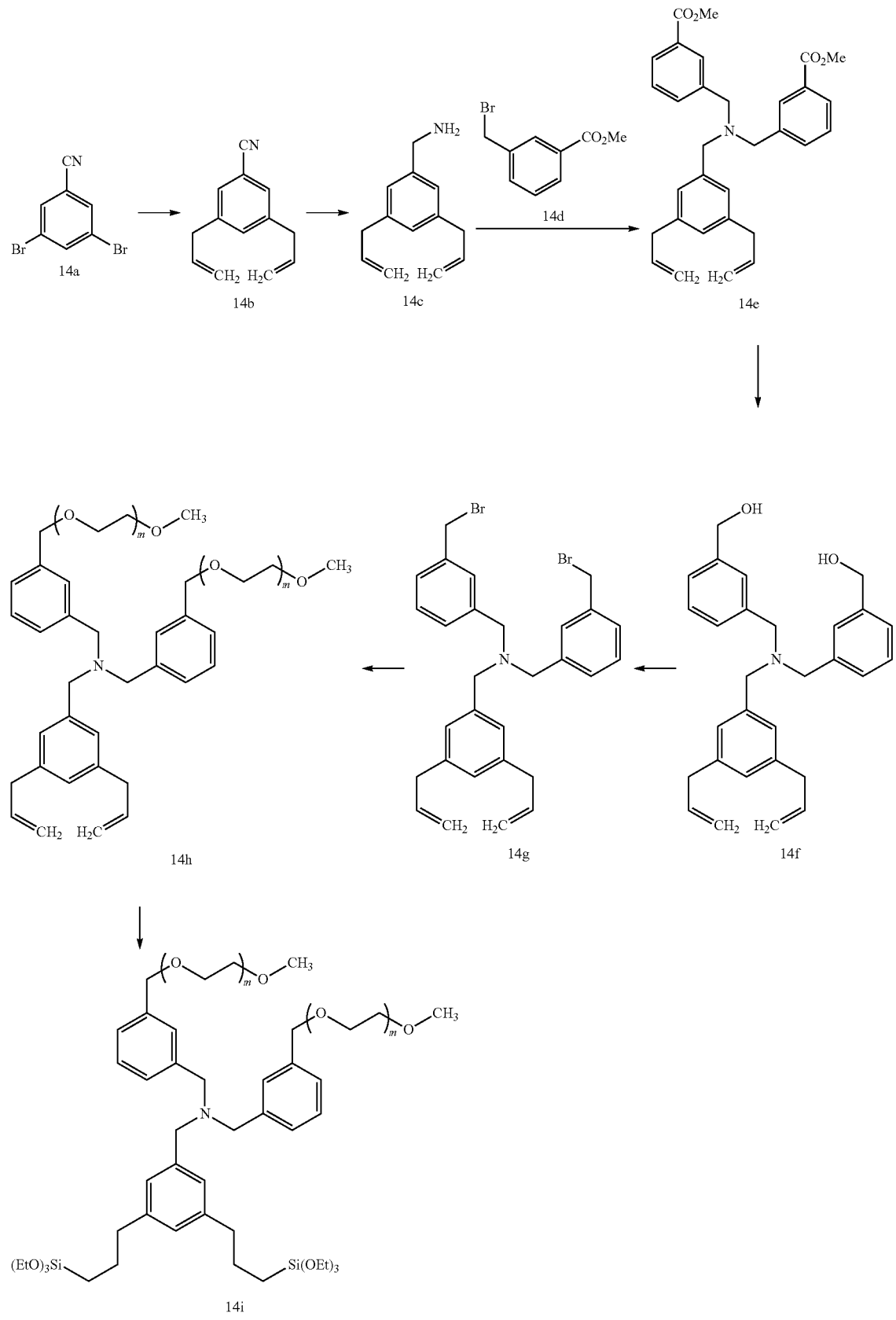

Compound 14b can be synthesized by allylation of 3,5-dibromobenzonitrile (14a) via a cross-coupling reaction, such as a Stille coupling. The cyano group can be selectively reduced by a suitable hydride source. The resulting amine 14c can be alkylated with two equivalents of methyl 3-methoxycarbonylbenzyl bromide (14d), followed by reduction of the ester by a suitable hydride source, e.g. LAH. The resulting alcohol 14f can be transformed to a leaving group such as halogen, bromide with a suitable reagent such as a halogenation reagent, e.g. $PBr_3$. A hydrophilic polymer with a suitable functionality, such as an alcohol, at one end, such as m-$PEG_{12-20}$-OH, can be deprotonated by a strong base, such as NaH, and can then give a nucleophilic substitution at the benzylic position to yield 14h. Finally the two vinyl groups can be hydrosilylated with a silane such as $(EtO)_3SiH$ and a catalyst, such as a platinum compound such as Karstedt's catalyst to yield the silane 14i.

Compound 15b can be synthesized by allylation of 4,4'-dihydroxybenzo-phenone (15a) via a nucleophilic substitution of an allylating reagent such as allyl bromide. The carbonyl group can be reduced by a hydride donor, followed by halogenation with a halogenation reagent such as $PBr_3$. The coupling with 15e protected on the alcohol functionalities by a base-stable protective group (PG), selected from the groups found in "Greene's Protective Groups in Organic Synthesis", 5th Edition, P. G. M. Wuts, Wiley, 2014, such as the tetrahydropyranyl group (THP), and a phosphonium ylide obtained by reaction of 15d with e.g. a phosphorous reagent such as $Ph_3P$ followed by treatment with a strong base, e.g. NaH, can provide 15f. Deprotection to remove both protective groups on the alcohols can be followed by coupling with a hydrophilic polymer carrying a suitable leaving group such as m-$PEG_{12-20}$-OMs (56). Finally, the two double bonds of 15h could be hydrosilylated with a

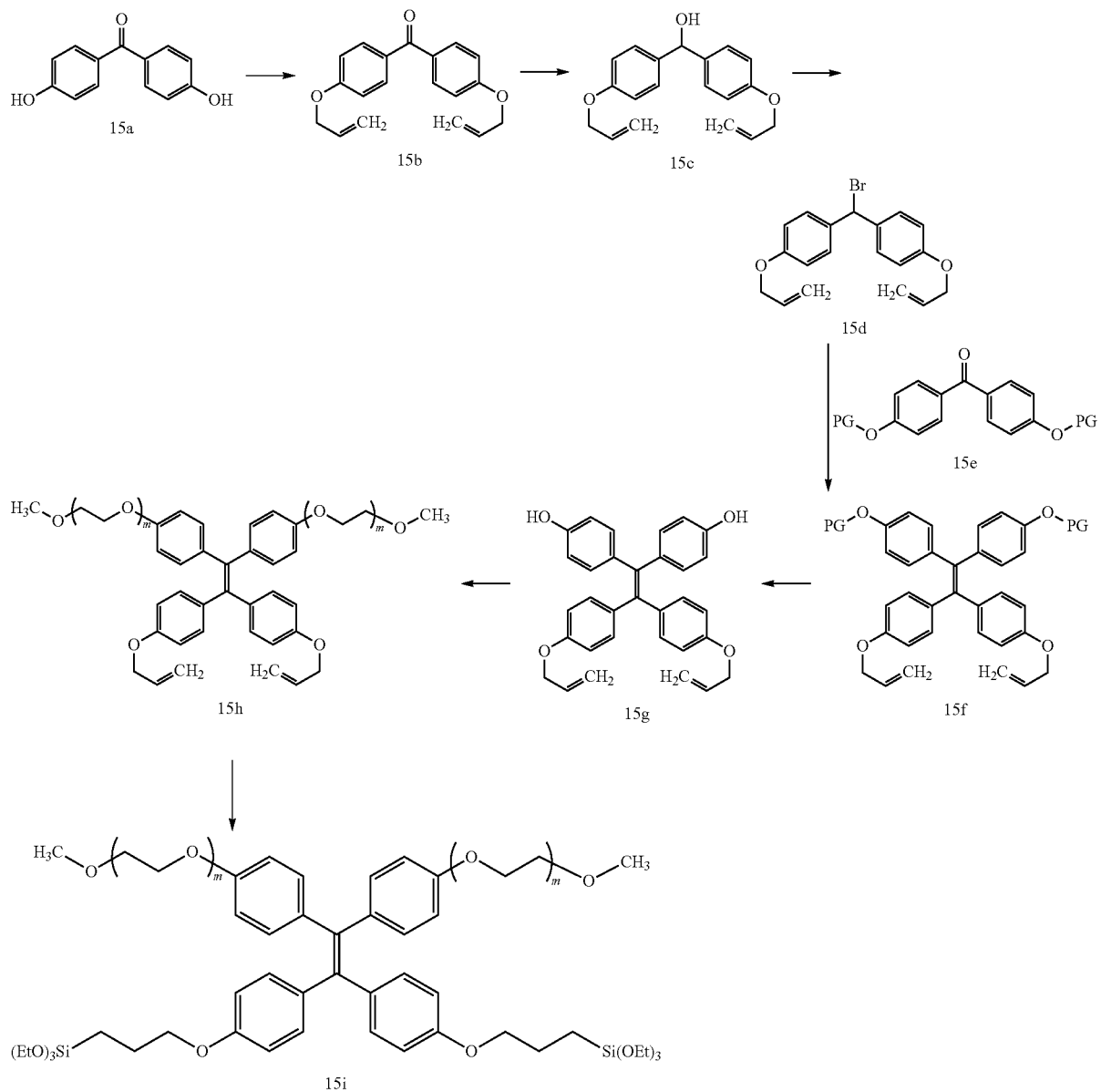

Scheme 15 silane such as (EtO)₃SiH and a catalyst, such as a platinum compound such as Karstedt's catalyst to yield 15i.

In some embodiments, the chemical structure (Formula 1) is as depicted in scheme 16, where X is methyl or lower alkyl, i.e. $C_{1-8}$, $R^1$-$R^6$ are independently selected from the group consisting of an alkoxy, aryloxy, halogen, dialkylamino, a nitrogen containing heterocycle or an acyloxy group, $A^1$ and $A^2$ are independently selected from the group consisting of $CH_2$, O or S, m is an integer from 6 to 25, $n^1$ is an integer from 1 to 3, $n^2$ is an integer from 1 to 3.

Scheme 16

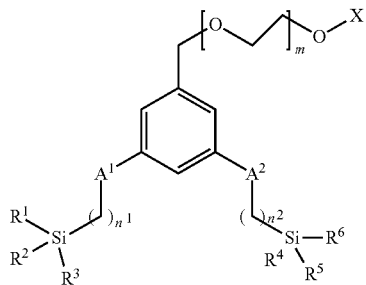

In some embodiments, the chemical structure is as depicted in scheme 16, where X is methyl, $R^1$-$R^6$ are methoxy or ethoxy, m is an integer from 12 to 20, n' and $n^2$ are both 3 and $A^1$ and $A^2$ are O.

In some embodiments, the chemical structure is as depicted in scheme 16, where X is methyl, $R^1$-$R^6$ are methoxy or ethoxy, m is an integer from 12 to 20, n' and $n^2$ are both 1 and $A^1$ and $A^2$ are $CH_2$.

Figure 2:
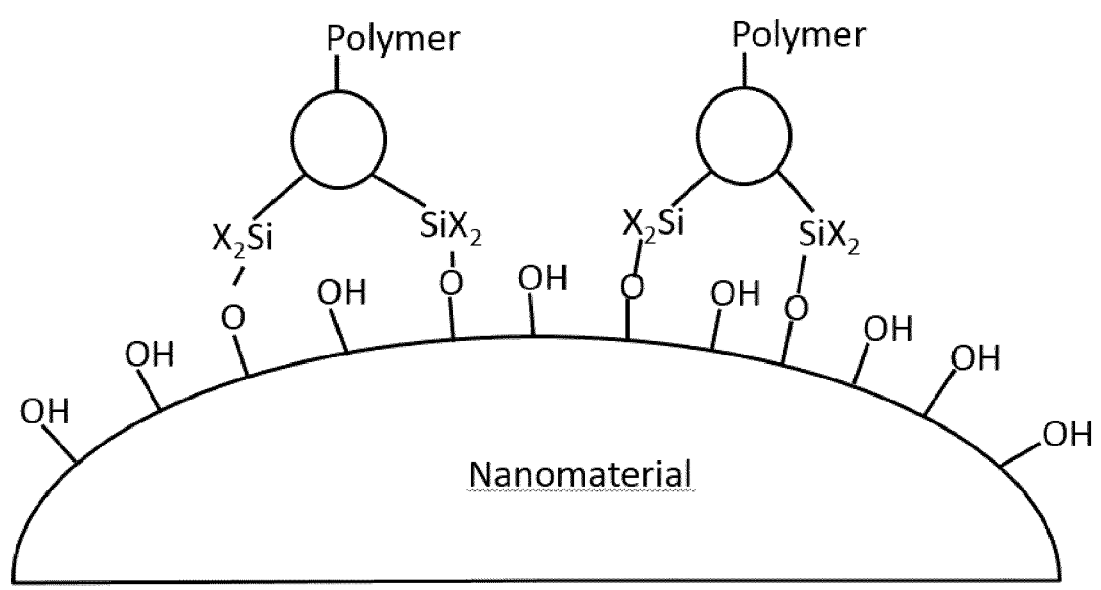
FIG. 2 is a schematic drawing of a part of a nanomaterial to which chemical compounds according to the present invention are attached.

Furthermore, the present disclosure relates to coated nanomaterials comprising hydrophilic polymer residues of said chemical compounds of scheme 1-16, where one or both of the activated silanes, to some extent, have formed covalent bonds with the surface of the uncoated nanomaterial, such as 1, 2, or more bonds, as shown in FIG. 2, where X is OH, O⁻, or a covalent bond to a surface bound oxygen.

The chemical compounds according to the invention may form bio-inert coatings of nanomaterials. The nanomaterials may carry suitable reactive groups on their surfaces. An example of such a reactive group is the hydroxyl group. In no way limiting but in particular is the Si—OH group suitable and also Fe—OH, Hf—OH, Zr—OH, Ta—OH and Ti—OH.

In some embodiments of the current invention, said nanomaterial is a nanostructure.

It is often advantageous to have a high coating density on the surface, such as more than 0.1 coating residues/nm² or more than 0.2 coating residues/nm² or more than 0.5 coating residues/nm² or more than 1 coating residue/nm², as has been achieved in the current invention (example 12). In particular is resistance to protein interaction dependent on achieving said high coating density.

In some embodiments the nanomaterial in FIG. 2 comprises Silicon atoms.

In some embodiments the nanomaterial in FIG. 2 comprises Phosphorus atoms.

In some embodiments the nanomaterial in FIG. 2 comprises Silicon and Phosphorus atoms.

In some embodiments the nanomaterial in FIG. 2 comprises Iron, Hafnium, Zirconium, Tantalum, Gadolinium, Terbium, Europium, or Titanium atoms.

In some embodiments the nanomaterials in FIG. 2 are nanostructures comprising a polymeric framework or scaffolding comprising chelating groups.

In some embodiments the nanomaterials in FIG. 2 are nanostructures comprising a polymeric framework or scaffolding comprising or adorned with at least five geminal bisphosphonate groups —P=O(OR¹)(OR²) wherein R¹ and R² are independently selected from a negative charge, H, alkyl and aryl.

In some embodiments the nanomaterials in FIG. 2 are nanostructures comprising paramagnetic manganese ions, incorporated in nanostructures based on a polymeric framework or scaffolding comprising chelating groups.

In some embodiments the nanomaterials in FIG. 2 are nanostructures comprising paramagnetic manganese ions, incorporated in nanostructures based on a polymeric framework or scaffolding comprising or adorned with at least five geminal bisphosphonate groups —P=O(OR¹)(OR²) wherein R¹ and R² are independently selected from a negative charge, H, alkyl and aryl.

In some embodiments the nanomaterials in FIG. 2 are nanostructures comprising paramagnetic manganese ions, incorporated in nanostructures based on a polymeric framework or scaffolding comprising or adorned with at least five geminal bisphosphonate groups —P=O(OR¹)(OR²) wherein R¹ and R² are independently selected from a negative charge, H, alkyl and aryl, and wherein the coating comprises covalently linked chemical structures of scheme 16 wherein X is methyl, one or more and of R¹-R³ and/or one or more of R⁴-R⁶ is a covalent bond to a surface oxygen of the nanostructure, wherein the remaining R¹-R³ and R⁴-R⁶ are methoxy, ethoxy, OH or O⁻; m is an integer from 6 to 25; n¹ and n² are 3; and A¹ and A² are O.

In some embodiments the nanomaterials in FIG. 2 are nanostructures comprising paramagnetic manganese ions, incorporated in nanostructures based on a polymeric framework or scaffolding comprising or adorned with at least five geminal bisphosphonate groups —P=O(OR¹¹)(O¹²) wherein R¹¹ and R¹² are independently selected from a negative charge, H, alkyl and aryl and wherein the coating comprises covalently linked chemical structures of scheme 16 where X is methyl, one or more of R¹-R³ and/or one or more of R⁴-R⁶ is a covalent bond to a surface oxygen of the nanostructure, wherein the remaining R¹-R³ and R⁴-R⁶ are methoxy, ethoxy, OH or O⁻; m is an integer from 12 to 20; n¹ and n² are 3; and A¹ and A² are O.

In some embodiments the coated nanomaterials or nanostructures comprise one or more handles for conjugation.

In some embodiments the coated nanomaterials or nanostructures comprise one or more conjugates.

In some embodiments the coated nanomaterials or nanostructures comprise one or more peptides as conjugates.

The present disclosure also relates to compositions, such as pharmaceutical compositions comprising a multitude of coated nanostructures according to the invention, and also to the use of such compositions of coated nanostructures as contrast agents or imaging agents of clinical utility, in particular use as contrast agents for MRI.

The coated nanostructures according to the invention, in their manganese or gadolinium loaded form, have the properties of low toxicity, with a tolerated dose of 400 μmol/kg in mice, and high relaxivity (25/mM/s) which makes them useful as contrast agents for MRI exams of organisms (or parts of organisms), such as a mammal, such as a human.

The combination of the properties of high relaxivity and of suitable size for those embodiments of the invention where the hydrodynamic diameter, as measured by DLS, is larger than 3 nm, or larger than 4 nm, or larger than 5 nm makes compositions comprising the coated nanostructures of the current invention suitable for imaging of tumors, in particular solid tumors by MRI. High relaxivity and good contrast provided in the current invention also enable the usage of said coated nanostructures as contrast agents for general anatomical imaging, e.g. angiography of the fine coronary arteries of the heart, carotid arteries, renal arteries, or the aorta.

In some embodiments of the current invention, a solution such as a pharmaceutically acceptable formulation of the coated nanostructures is administered to a subject such as a human by a parenteral route such as intravenously, and the subject is subjected to an MRI investigation.

Imaging of structures in the head, internal organs such as liver, pancreas and bowels, or extremities are also of interest. Imaging of the colon can be achieved either by intravenous administration. For imaging of the stomach, liver and the upper gut it is conceivable to administer the contrast agent orally.

Since the coated nanostructures of the current invention have the properties of high relaxivity and low toxicity it is conceivable to use the material for cell tagging. In that case cells e.g. stem cells or macrophages are loaded with the coated nanostructures externally to a mammalian body, e.g. a human body, and then inserted into said mammal and an image is generated by MRI scanning. It is then possible to follow the cells as they are transported through the organism.

The in-vivo use of the coated nanostructures of this invention requires them to be formulated in a pharmacologically acceptable way according to best practice well known to those skilled in the art. The preferred mode of administration is parenteral, in particular is the intravenous route advantageous. However, intra-arterial administration may have advantages under certain circumstances, such as when a high local contrast is desired. Parenteral administration often requires a liquid formulation. Water is a preferred solvent to bring the coated nanostructures of the current invention into solution but one or more co-solvents or additives may be added in 0.1-10% (vol/vol) to improve the stability of the solution. Acceptable co-solvents are alcohols like ethanol or glycerol; biocompatible polymers like polyethyleneglycol or polyvinyl alcohol; dimethyl sulfoxide; or N-methyl pyrrolidinone. It can also be advantageous to add one or more osmoregulators like sodium chloride, mannitol, sorbitol, lactose, glucose or other sugars or sugar alcohols. It is desirable that the formulation is isoosmotic or somewhat hyperosmotic to the body fluids. Preferably, the solution for intravenous use has an osmolality from 270-2000 mOsm, or 280 to 1000 mOsm, or 280 to 500 mOsm. Many of said additives may also fulfill the function of cryoprotectants, enhancing the efficiency of reconstitution after freeze drying. It may also be advantageous to add electrolytes to lower the physiological effects of the injected solution. Preferred electrolytes are a combination of non toxic salts of sodium, calcium or and/or magnesium. Regulation of the pH of the injectable solution is preferable and any buffer suitable for injection can be contemplated. A preferred buffer is Tris-HCl. Antioxidants such as, but not limited to, sulfite, dithionite and/or thiosulfate may also be added to improve shelf-life of the composition.

The concentration of nanostructures may be described in many different ways but the two most relevant are mass concentration given as g/l solution and concentration of manganese in mmol/l solution. Concentration ranges of manganese in formulations that are suitable for administration as a contrast agent range from 1-500 mM, or 10-300 mM, or 10-200 mM, or 10-100 mM or 20-80 mM. When given as a mass concentration and assuming that the phosphorus to manganese ratio is around 10, the mass concentrations that are suitable for contrast agent formulation range from 0.5-300 g/l, or 25-300 g/l, or 50 to 300 g/l, or 100-300 g/l.

One embodiment of the current invention constitutes a pharmaceutically acceptable formulation of a multitude of nanostructures according to the current invention for intravenous administration with a manganese concentration between 10 and 100 mM and a phosphorus to manganese molar ratio of 7-20.

One embodiment of the current invention constitutes a pharmaceutically acceptable formulation of a multitude of nanostructures according to the current invention for intravenous administration with a manganese concentration between 40 and 80 mM and a phosphorus to manganese molar ratio of 7-15.

Some embodiments of the current invention constitute compositions comprising a multitude of coated nanostructures according to the current invention.

In some embodiments of the current invention the coated nanomaterials or coated nanostructures comprise a diagnostically useful radioactive isotope such as a gamma emitting isotope suitable for SPECT imaging such as $^{99}$Tc or a positron emitting isotope suitable for PET imaging such as $^{68}$Ga.

The present invention further relates to a method to produce said coating chemical compounds according to the current invention. There are many options conceivable to one skilled in the art, for the production of said chemical structures, however, due to the sensitive nature of the activated silanes, they should be introduced late in the process, such as in the last step.

The chemical structures according to the present invention may be obtained by a method that comprises hydrosilylation as the last chemical step.

According to one embodiment of the present invention, the method for obtaining the chemical compounds according to the invention comprises an extractive separation step in the penultimate chemical step.

According to another embodiment, the method may comprise a sequence of operations involving extraction with a hydrocarbon, adding an inorganic salt, and an extraction with a polar water immiscible solvent such as ethyl acetate in the penultimate chemical step.

Furthermore, the present disclosure relates to a method for producing the coated nanomaterials or nanostructures according to the invention. In general, this involves providing the uncoated nanomaterial or nanostructure in a suitable solvent, such as a polar solvent such as a solvent comprising water or an alcohol such as ethylene glycol or an aprotic polar solvent such as dimethylformamide or dimethyl sulfoxide, as a suspension or a solution. In a second step, a chemical compound according to the invention (a coating precursor) is contacted with said solution or suspension and, optionally, in the presence of an additive or adjusting the pH away from neutral, followed by heating the resultant mixture for a specified time. When the purpose is to produce a MRI contrast agent, a step of adding a manganese source, e.g. a manganese(II) salt, e.g. manganese(II)chloride, is introduced. The inventors have found, see example 19, that a much better yield of coated nanostructures may be obtained if urea, ammonium carbonate, or ammonia is used as an additive during the coating process. The highest yields are obtained in the presence of urea. The improvement can be as great as a factor of 20. The inventors have also found that the yield of coated nanostructures is improved when the coating precursor is added slowly, such as over several hours such as from 5 to 20 hours. We have found that to obtain the best manganese chelating ability of the final coated nanostructures the reaction mixture should be heated for a prolonged period of time such as 24-168 h, or 48-120 h, or 80-110 h at a temperature of 80-120° C., or 90-100° C.

The method of coating nanostructures may be performed with urea as an additive.

The method of coating nanostructures may be performed with urea as an additive at a concentration of between 0.1 and 1 M.

The method of coating nanostructures may be performed with urea as an additive at a concentration of between 0.4 and 0.6 M.

The method of coating nanostructures may be performed with ammonium carbonate or ammonia as an additive at a concentration of between 0.1 and 1 M.

The method of coating nanostructures may be performed with a mixture of water and ethylene glycol as solvent.

The method of coating nanostructures may be performed so that the coating precursor is added over several hours.

The method of coating nanostructures may be performed so that the coating precursor is added over 5-20 hours.

The method of coating nanostructures may be performed so that the coating precursor is added over 8-12 hours.

The method of coating nanostructures may be performed so that the coating precursor is added at a temperature between 80 and 100° C.

The method of coating nanostructures may be performed so that after the coating precursor has been added the temperature is kept between 90 and 110° C. for between 80 and 120 h.

The nanostructures may be purified by filtration such as tangential flow filtration.

The nanostructures may be purified by tangential flow filtration, first through a filter with large pores to remove undesirably large impurities and then collected as a retentate solution on a small pore filter where solvent residues and small molecule impurities are removed.

The nanostructures may be purified by tangential flow filtration, first through a filter with a nominal cut-off value of 50 to 100 kDa to remove undesirably large impurities and then collected as a retentate solution on a filter with a nominal cut-off of value 10 kDa or smaller where solvent residues and small molecule impurities are removed.

SPECIFIC EMBODIMENTS

1. A chemical compound comprising a core, at least one hydrophilic polymer residue and at least two anchoring groups each anchoring group comprising an activated silane group.
2. A chemical compound according to embodiment 1, wherein the core is an aromatic core.
3. A chemical compound according to embodiment 1, wherein the core is a carbocyclic, non-aromatic, core.
4. A chemical compound according to embodiment 3, wherein the core is a heterocycle.
5. A chemical compound according to any one of embodiments 1 to 4, wherein the anchoring groups have the anchoring groups have the following general formula -A-$(CH_2)_n$$SiY_3$ wherein A is a covalent bond, $CH_2$, or O, "n" is an integer from 1 to 3, and Y is independently selected from the group consisting of an alkoxy group, an aryloxy group, a halogen, a dialkylamino group, a nitrogen-containing heterocycle and an acyloxy group, wherein the at least two anchoring groups may be the same or different.
6. A chemical compound according to any one of embodiments 1 to 5, wherein the hydrophilic polymer residue is PEG (polyethylene glycol).
7. A chemical compound according to any one of embodiments 1 to 5, wherein the hydrophilic polymer residue is mPEG (methyl terminated polyethylene glycol).
8. A chemical compound according to embodiment 6 or 7, wherein the hydrophilic polymer residue has a chain length of 10-500 ethylene glycol residues.
9. A chemical compound according to embodiment 6 or 7, wherein the hydrophilic polymer residue has a chain length of 10-50 ethylene glycol residues.
10. A mixture of chemical compound according to embodiment 6 or 7, wherein the chain lengths of the hydrophilic polymer residues are between 6 and 25, with 16 being the most abundant, ethylene glycol residues.
11. A coated nanostructure comprising residues of the chemical compounds according to any one of embodiments 1 to 9, wherein one or both of the activated silanes in each of the chemical compounds, has been covalently bonded to the surface of the nanostructure core.
12. A coated nanostructure comprising a mixture according to embodiment 10, wherein one or both of the activated silanes in each of the chemical compounds, has been covalently bonded to the surface of the nanostructure core.
13. A coated nanostructure according to embodiment 11 or 12, wherein the nanostructure comprises a polymeric framework comprising, or adorned with, monomer residues containing a geminal bisphosphonate group and two organo-oxysilane groups.
14. A coated nanostructure according to embodiment 11 or 12, wherein the nanostructure comprises a polymeric framework comprising, or adorned with, at least five geminal bisphosphonate groups having the general formula —P=O$(OR^{11})(OR^{12})$, wherein $R^{11}$ and $R^{12}$ are independently selected from a negative charge, H, an alkyl group and an aryl group, wherein the polymeric framework further comprises monomer residues containing a geminal bisphosphonate group and two organo-oxysilane groups.
15. A coated nanostructure according to any one of embodiments 11 to 14, wherein the hydrodynamic diameter of the coated nanostructure is 2-50 nm.
16. A coated nanostructure according to any one of embodiments 11 to 14, wherein the hydrodynamic diameter of the coated nanostructure is 3-10 nm.
17. A coated nanostructure according to any one of embodiments 11 to 14, wherein the hydrodynamic diameter of the coated nanostructure is 3-7 nm.
18. A coated nanostructure according to any one of embodiments 11 to 14, wherein the hydrodynamic diameter of the coated nanostructure is 10-50 nm.
19. A coated nanostructure according to any one of embodiments 11 to 14, wherein the hydrodynamic diameter of the coated nanostructure is 10-20 nm.
20. A coated nanostructure according to any one of embodiments 11 to 19, further comprising a manganese(II) or a gadolinium(III) ion.
21. A coated nanostructure according to embodiment 20, wherein the P/Mn molar ratio is 5-20.
22. A coated nanostructure according to embodiment 20 or 21, wherein the Si/Mn molar ratio is 4-20.

23. A coated nanostructure according to any one of the embodiments 20 to 22, wherein the nanostructure comprises a polymeric framework comprising, or adorned with, monomer residues containing a geminal bisphosphonate group and wherein the manganese ions are coordinated to the phosphonate groups.
24. A coated nanostructure according to any one of embodiments 11 to 19, further comprising a radionuclide for imaging and/or radiotherapy.
25. A method for obtaining a coated nanostructure according to any one of embodiments 11 to 19, comprising the steps of
    providing a nanostructure; and
    contacting said nanostructure with at least one of the chemical compounds according to any one of embodiments 1 to 9 or with a mixture according to embodiment 10.
26. A method for obtaining a coated nanostructure according to any one of embodiments 20 to 23, comprising the steps of
    providing a nanostructure comprising a polymeric framework comprising, or adorned with, monomer residues containing a geminal bisphosphonate group;
    contacting said nanostructure with at least one of the chemical compounds according to any one of embodiments 1 to 9 or with a mixture according to embodiment 10; and
    contacting said nanostructure with manganese ions or gadolinium ions.
27. A method according to embodiment 25 or 26, further comprising a step wherein the nanostructures are purified by ultrafilatration.
29. A method for obtaining a coated nanostructure according to embodiment 24, comprising the steps of
    providing a nanostructure comprising geminal bisphosphonate groups;
    contacting said nanostructure with at least one of the chemical compounds according to any one of embodiments 1 to 9 or with a mixture according to embodiment 10; and
    contacting said nanostructures with a radionuclide for imaging and/or radiotherapy.
30. A method according to embodiment 29, further comprising a step wherein the nanostructures are purified by ultrafilatration.
31. A composition comprising a coated nanostructure according to any one of embodiments 11 to 19.
32. A composition comprising a coated nanostructure according to any one of embodiments 20 to 23.
33. A composition comprising a coated nanostructure according to embodiment 24.
34. Use of a coated nanostructure according to any one of embodiment 20 to 23 or a composition according to embodiment 32 as a MRI contrast agent.
35. Use of a coated nanostructure according to embodiment 24 or a composition according to embodiment 33 as a PET and/or SPECT imaging agent.
36. Use of a coated nanostructure according to embodiment 24 or a composition according to embodiment 33 in radiotherapy.
37. A coated nanostructure according to any one of embodiment 20 to 23 or a composition according to embodiment 32, for use as an MRI contrast agent.
38. A coated nanostructure according to embodiment 24 or a composition according to embodiment 33, for use in PET and/or SPECT imaging.
39. A coated nanostructure according to embodiment 24 or a composition according to embodiment 33, for use in radiotherapy.

EXAMPLES

General Experimental Details

SIR-200 was purchased from Resintech, USA (resintech.com) and activated by $Na_2S$, carefully washed and dried before use.

Acronyms: Dimethyl formamide (DMF), tetrahydrofuran (THF), dichloromethane (DCM), polytetrafluoroethylene (PTFE), ethyl acetate (EtOAc), methanol (MeOH), ethanol (EtOH), potassium acetate (KOAc), acetonitrile (MeCN), lithium aluminum hydride (LAH).

Example 1: Synthesis of Compound 6, 1-[ω-methyl-(ethyleneoxy)$_{12-20}$ methyl]-3,5-bis[(prop-3-triethoxysilyl-1-yl)oxy]benzene

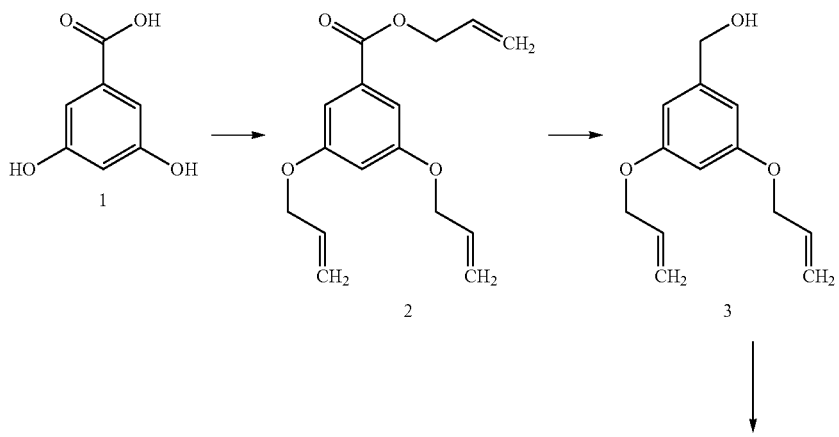

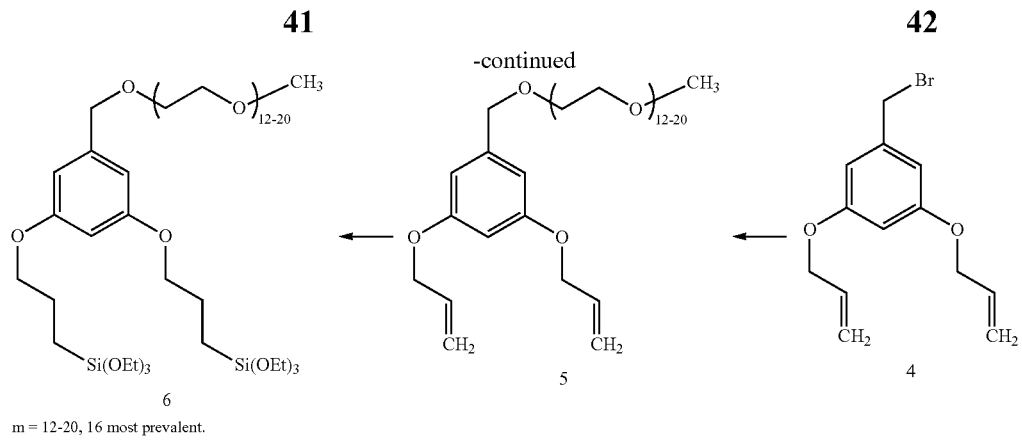

m = 12-20, 16 most prevalent.

Example 1a: Compound 2, 3,5-diallyloxy Allylbenzoate 3,5-dihydroxy benzoic acid (1) (100 g, 0.65 mol) was dissolved in DMF (500 ml), under nitrogen, in a 2 L reactor stirred with a 4 blade stainless steel stirrer. Potassium carbonate (345 g, 2.5 mol, Fw=138.2 g/mol) was added by spoon, trying to avoid caking. The temperature rose from 22 to 34° C. and the mixture got thick. The reactor was fitted with a spiral condenser and the jacket temperature was set to 50° C. Allyl bromide (344 g, 246 ml, 2.85 mol, d=1.40 g/ml, Mw=121 g/mol) was filled in a 250 ml pressure equalizing dropping funnel and fitted to the reactor. When the inner temperature had reached 47° C., addition was started with 25 ml portions for the first 150 ml and then 50 ml portions. The inner temperature was allowed to peak (50 to 57° C. and fall back a degree or to 55° C. before the next addition. Total addition time 2 h 15 min. The reaction mixture was left stirring with a jacket temperature of 50° C. until next day. The slurry was removed through the bottom valve (washed out with 60 ml DMF) and collected in a 1 L bottle and passed through a glass fiber filter on a Büchner funnel. The cake was washed with 3×60 ml DMF. The reactor was cleaned with water and the DMF solution was reintroduced. The reactor was fitted with a distillation head with an efficient vertical spiral condenser. The pressure was reduced in the reactor (central vacuum, about 20 mbar) and the DMF was distilled off at a brisk pace with a jacket temperature gradually increased from 70 to 85° C., liquid temperature from 53-75° C. and a vapor temperature of 50-53° C. The byproduct allyl potassium carbonate precipitates as an oil as the DMF is removed. The residue was drained through the bottom valve while still warm and collected in a 500 ml RB flask. The allyl carbonate solidifies to lumps when left in the fridge overnight. The oil/solids were transferred to 4×50 ml centrifuge tubes and centrifuged. The supernatant product was decanted. Yield 142 g, 518 mmol, 80%. $^1$H NMR (400 MHz, CDCl$_3$): δ=7.23 (s, 2H), 6.70 (s, 2H), 6.05 (m, 3H), 5.42 (m, 3H), 5.30 (m, 3H), 4.81 (d, J=5.58 Hz, 2H), 4.55 (d, J=5.20 Hz, 4H).

Example 1b: Compound 3, 3,5-diallyloxy Benzylalcohol

A 2 l jacketed reactor was fitted with an efficient condenser and a PTFE coated two blade stirrer. The cooling spiral of the condenser was connected to an independent silicon oil temperature controller. The system was dried out under vacuum with the jacket temperature set to 130° C. for a few hours and then the system was filled with nitrogen and allowed to cool. Dry methyl t-butyl ether (MTBE, 1.5 l) was cannulated into the reactor trough a silicone septum. Pellets of lithium aluminum hydride (20 g, 0.158 mol, Fw=37.95) were added, first one checking that there is only minor moisture in the system and then the rest. The temperature rose about one degree. The pellets don't dissolve. The ester of example 1a (210 g, 0.766 mol) was dissolved in dry MTBE (500 ml) under nitrogen in an addition funnel. The addition funnel was fitted to the reactor. The jacket temperature was set to 28° C. and the condenser temperature was set to 5° C. When the inner temperature reached 25° C. the starting material was added in small portions through the addition funnel. The reaction is highly exothermic and the temperature rises immediately after each addition. As soon as the temperature has peaked the next small portion can be added. The addition took 2 h and the maximum temperature was 34° C. After 1 h stirring the jacket temperature was set to 0° C. and when the inner temperature reached 5° C. water (20 ml) was added very carefully (3×0.1, 0.2, 0.2, 0.3, 0.3, 0.4, 0.4, 0.5, 0.5, 4×0.6, 3×1, 1.5, 5, 5 ml). The reaction with the first drops is very violent. The temperature was allowed to go down to 5° C. after each portion. Total addition time 1 h 10 minutes. No LiAlH$_4$ pellets were visible before moving on. 20 ml of 15% (w/v) aqueous NaOH were added followed by another 60 ml of water. The suspension was stirred for 15 min and then temperature was set to 20° C. and the mixture was stirred for another 20 minutes. A white granular precipitate was formed. Anhydrous MgSO$_4$ (150 g) was added and the resulting mixture was stirred for another hour. The slurry was drained through the bottom valve and filtered on glass fiber filter (GF/A). The cake was washed twice with 300 ml MTBE and the combined filtrates were evaporated on a rotary evaporator. Yield 161.7 g, 96%. $^1$H NMR (400 MHz, CDCl$_3$): δ=6.54 (bs, 2H), 6.43 (s, 1H), 6.05 (m, 2H), 5.42 (d, J=17.69 Hz, 2H), 5.29 (d, J=9.65 Hz, 2H), 4.62 (s, 2H), 4.52 (d, J=5.15 Hz, 4H).

Example 1c: Compound 4, 3,5-diallyloxy Benzylbromide

A 2 l jacketed reactor with temperature controller was fitted with a septum and a PTFE coated two blade stirrer. The system was filled with nitrogen and the diallyloxy benzylalcohol 3 of example 1 b (42.2 g, 0.192 mol) in DCM (500 ml) was introduced into the reactor. The temperature controller was set to 0° C. and, when the inner temperature reached 2° C., PBr$_3$ (22.3 ml, 64.3 g, 0.238 mol, 1.24 eq, Mw=270.69) was added in portions with a syringe through the septum. The reaction is moderately exothermic but temperature should not rise above 5° C. Total addition time 30 minutes. After 5 minutes the reaction was quenched by the addition of solid NaHCO$_3$ (36 g, 0.43 mol Fw: 84.01). The temperature rose from 1 to 12° C. with a slow start. After 30 minutes 22 g of anhydrous MgSO$_4$ was added and then 90 g of silica. The mixture was siphoned off (silica damages the bottom valve if used) and filtered through a glass fiber filter. The filter cake was washed with 2×100 ml DCM. and evaporated with a bath temperature of 20° C. The product is temperature sensitive, kept in fridge or freezer. The product was obtained as a brown oil (50 g, 0.177 mol, 92% yield. $^1$H NMR (400 MHz, CDCl$_3$): δ=6.56 (d, J=2.29 Hz, 2H), 6.44 (t, J=2.05 Hz, 1H), 6.05 (m, 2H), 5.42 (dq, J=17.10, 0.95 Hz, 2H), 5.30 (dq, J=10.13, 1.90 Hz, 2H), 4.52 (dt, J=5.13, 1.71 Hz, 4H), 4.41 (s, 2H).

Example 1d: Compound 5, 1-[ω-methyl-(ethyleneoxy)$_{12-20}$ methyl]-3,5-bis[(prop-2-en-1-yl)oxy]benzene As a preparation, m-PEG$_{12-20}$-OH (polydisperse) was dried by heating to 40° C. under vacuum overnight in a round bottom flask. The reactor was dried out under vacuum with the jacket temperature set to 130° C. for 1 h and then the system was filled with nitrogen and allowed to cool. NaH (10.1 g, 0.25 mol, 60% in mineral oil, 1.1 eq) was loaded into the reactor followed by THF (230 ml, anhydrous) which was transferred from a sure-seal bottle to the reactor via a double ended needle. The temperature controller was set to 0° C. When the inner temperature was below 2° C., a solution of m-PEG$_{12-20}$-OH (173.9 g, 0.23 mol, 1.0 eq) in THF (115 ml, anhydrous) was added dropwise over 15 minutes with the temperature rising up to 7° C. Stirring was continued for 1 h more and then the temperature controller was set to 10° C. A solution of the diallyloxy benzylbromide of example 1c (65 g, 0.23 mol) in THF (45 ml, anhydrous) was filled in an addition funnel. The addition funnel was fitted to the reactor and the solution was added over 15 minutes. The inner temperature rose to 17° C. The temperature controller was set to 18° C. and stirring was continued for other 2 hours. Thereafter the reaction mixture was cooled down to 5° C. and the reaction was quenched by dropwise addition of 0.1 M HCl solution (230 ml) reaching a pH of 5.5. The mixture was allowed to warm up to room temperature followed by the evaporation of the organic solvent. The crude was diluted with water up to the volume of 800 ml. Solid NaCl (32.5 g) was added followed by the addition of heptane (200 ml) and toluene (30 ml) and resulting mixture stirred for 15 minutes. The organic phase was removed and extraction procedure repeated other 3 times. The water phase was then extracted with EtOAc (200 ml×3). The combined EtOAc phases were dried with MgSO$_4$, filtered and evaporate yielding compound 5 (170 g, 78% yield) as a yellowish gel. $^1$H NMR (400 MHz, CDCl$_3$): δ=6.52 (d, J=1.98 Hz, 2H), 6.42 (s, 1H), 5.41 (d, J=17.13 Hz, 2H), 5.28 (d, J=10.28 Hz, 2H), 4.51 (m, 6H), 3.71-3.58 (m, 54H), 3.55 (m, 2H), 3.38 (s, 3H).

Example 1e: Compound 6, 1-[ω-methyl-(ethyleneoxy)$_{12-20}$ methyl]-3,5-bis[(prop-3-triethoxysilyl-1-yl)oxy]benzene A 2 l jacketed reactor with temperature controller was fitted a septum and a PTFE coated two blade stirrer. The system was filled with nitrogen and 3,5-diallyloxybenzyloxy PEG 5 of example 1d (170.0 g, 178.3 mmol) and dry toluene (700 ml, needle transfer) and triethoxysilane (136.9 ml, 121.9 g, 0.713 mol, 4.0 eq). The bath temperature was set to 40° C. Karstedt's catalyst (5 ml, 2% in xylenes). Temperature peaked at 59° C. When the temperature had returned to 40° C. more catalyst solution (1.0 ml) was added and no temperature change was observed. Left overnight at room temperature. $^1$H NMR of the crude showed the disappearance of the olefinic protons and the appearance of the triethoxysilyl group in the molecule. The solvent was then evaporated and excess silane was driven off by evaporating with anhydrous toluene (60 ml). The product was dissolved in toluene (400 ml) degassed with 3 cycles of vacuum/nitrogen and stirred with activated SIR-200 (180 g) for 4 days. Filtration and evaporation gave 190.0 g (148.7 mmol, 83% yield) of 6 as a pale oil (99% yield), which was used directly for coating experiments.

Example 2: Synthesis of Compound 14, 5,5'-bis[ω-methyl-(ethyleneoxy)$_{12-20}$ methyl]-3,3'-bis[(prop-3-triethoxysilyl-1-yl)oxy]-1,1'-biphenyl

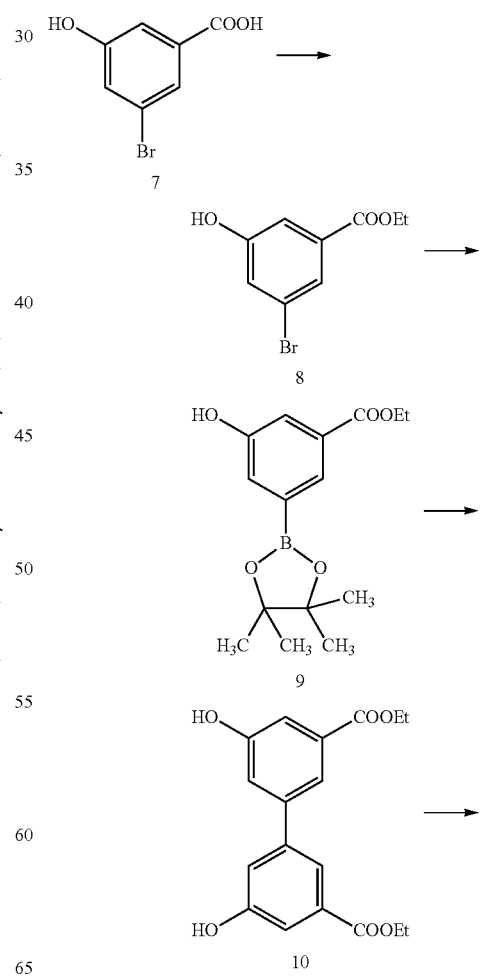

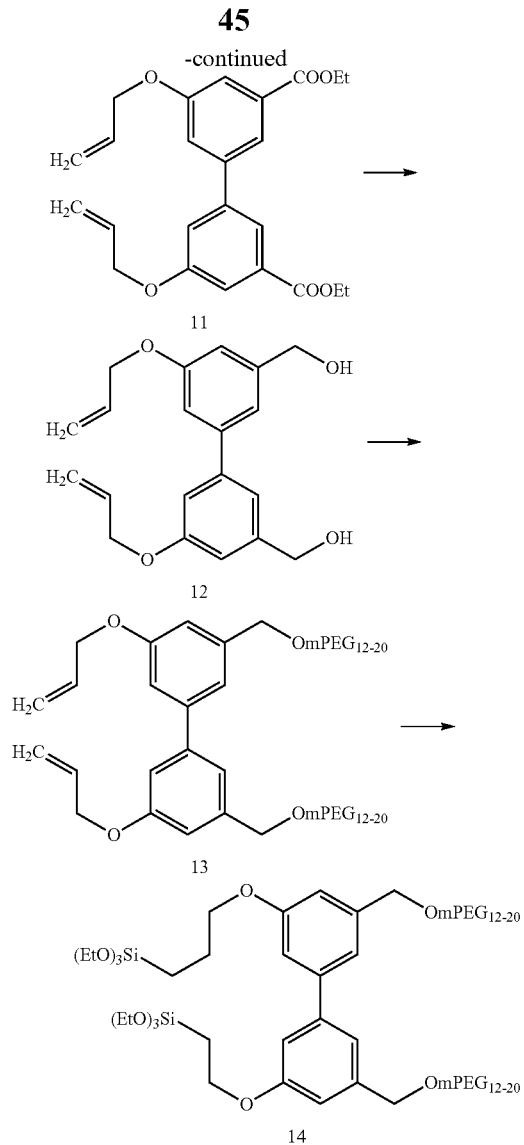

Example 2a: Compound 8, 3-Bromo-5-hydroxybenzoic Acid Ethyl Ester

To a solution of 7 (1.00 g, 4.38 mmol) in EtOH (9 ml), SOCl$_2$ (1.08 g, 0.80 ml, 8.76 mmol, 2.0 eq) was added dropwise at 0° C. When the addition was completed the reaction mixture was allowed to warm up to room temperature and stir overnight. The solvent was then removed under reduced pressure and the yellow residue was passed through a short pad of silica (heptane:EtOAc=20:1) to obtain the desired product 8 as white crystals (1.06 g, 4.32 mmol, 99% yield). $^1$H and $^{13}$CNMR in agreement with literature reference [Tetrahedron 2016, 72, 3567-3578].

Example 2b: Compound 9, 3-hydroxy-5-(4,4,5,5-tetramethyl-1,3,2-dioxaborolan-2-yl)benzoic Acid Ethyl Ester A flame dried Schlenk flask, was charged with 8 (1.68 g, 6.88 mmol), bis(pinacolato)diboron (1.94 g, 7.57 mmol, 1.1 eq), PdCl$_2$(dppf).DCM (281.1 mg, 0.34 mmol, 0.05 eq) and KOAc (2.05 g, 20.65 mmol, 3.0 eq) under nitrogen atmosphere, followed by dry and degassed dioxane (35 ml). The resulting mixture was heated up to 80° C. for 20 h. After cooling it down to RT it was filtered through a pad of celite with the help of EtOAc and the resulting residue purified by a short flash chromatography (heptane:EtOAc=4:1) to obtain the desired product 9 in quantitative yield as yellowish solid. $^1$H NMR (400 MHz, CDCl$_3$): δ=8.04 (s, 2H), 7.63 (s, 2H), 7.46 (s, 1H), 4.38 (q, J=7.07 Hz, 2H), 1.40 (t, J=7.07 Hz, 3H), 1.36 (s, 12H).

Example 2c: Compound 10, 3,3'-diethoxycarbonyl-5,5'-dihydroxy-1,1'-biphenyl

In a flame dried Schlenk flask, 9 (2.01 g, 6.88 mmol) was dissolved in anhydrous THF (30 ml), and 8 (1.83 g, 7.48 mmol, 1.1 eq) was added to the solution. Pd(PPh$_3$)$_4$ (0.803 g, 0.69 mmol, 0.1 eq) and an aqueous degassed 2 M K$_2$CO$_3$ (13.8 ml, 27.5 mmol) solution were sequentially added thereto, and the mixture was refluxed for 48 h. DCM (15 ml) was added and the aqueous layer was extracted with DCM twice. After drying with MgSO$_4$, the product was purified by flash chromatography (heptane:EtOAc=3:2) to provide 10 (1.92 g, 5.81 mmol, 84% yield) as a white solid. $^1$H NMR (400 MHz, DMSO-d6): δ=10.05 (s, 2H), 7.58 (s, 2H), 7.38 (s, 2H), 7.25 (s, 2H), 4.33 (q, J=7.25 Hz, 4H), 1.33 (t, J=7.07 Hz, 6H).

Example 2d: Compound 11, 3,3'-Diallyloxy-5,5'-diethoxycarbonyl-1,1'-biphenyl To a suspension of the diol 10 (630.0 mg, 1.91 mmol) and K$_2$CO$_3$ (1.33 g, 9.54 mmol, 5.0 eq) in dry MeCN (7 ml), was added allyl bromide (0.67 ml, 7.63 mmol, 4.0 eq) and the resulting solution was refluxed for 20 h and then filtered through celite, washing with EtOAc. After solvent evaporation the residue was passed through a short silica pad (heptane:EtOAc=3:2) to get 12 (767.0 mg, 1.87 mmol, 98% yield) as a colourless oil. $^1$H NMR (400 MHz, CDCl$_3$): δ=7.89 (s, 2H), 7.60 (s, 2H), 7.36 (s, 2H), 6.15-6.05 (m, 2H), 5.48 (d, J=17.15 Hz, 2H), 5.35 (d, J=10.61 Hz, 2H), 4.66 (d, J=5.30 Hz, 4H), 4.42 (q, J=7.07 Hz, 4H), 1.43 (t, J=7.25 Hz, 6H).

Example 2e: Compound 12, 3,3'-Diallyloxy-5,5'-dihydroxymethyl-1,1'-biphenyl

To a solution of 11 (500.0 mg, 1.22 mmol) in toluene (15 ml), Red-Al (1.59 ml, 4.87 mmol, 4.0 eq) was added at 0° C. under nitrogen atmosphere. After stirring for 1 h, the reaction was quenched according to the Fieser work up (J. Org. Chem. 1953, 18, 1190). The collected filtrate was passed on a short silica pad (heptane:EtOAc=1:1→1:4) to obtain 12 (332.0 mg, 1.02 mmol, 83% yield) as a white solid. $^1$H NMR (400 MHz, CDCl$_3$): δ=7.18 (s, 2H), 7.07 (s, 2H), 6.95 (s, 2H), 6.14-6.05 (m, 2H), 5.45 (d, J=17.2 Hz, 2H), 5.32 (d, J=10.6 Hz, 2H) (q, J=7.07 Hz, 2H), 4.74 (s, 4H), 4.61 (d, J=4.5 Hz, 4H).

Example 2f: Compound 13, 5,5'-bis[ω-methyl(ethylenoxy)$_{12-20}$ methyl]-3,3'-[(prop-2-en-1-yl)oxy]-1,1'-biphenyl To a solution of 12 (70.0 mg, 0.214 mmol) in THF (1.0 ml), NaH (21.4 mg, 0.536 mmol, 2.5 eq) was added at 0° C. and the resulting suspension stirred for 30 minutes after which a solution of 56 of example 16 (340.8 mg, 0.407 mmol, 1.9 eq) in THF (1.0 ml) was added at the same temperature. The reaction mixture was then allowed to warm up to room temperature and stir overnight. The suspension was then quenched with H₂O (0.1 ml) and the solvent evaporated. The resulting oil was purified by flash chromatography (DCM→DCM:MeOH=95:5) to get 13 as an orange oil (222.3 mg, 58% yield). $^1$H NMR (400 MHz, CDCl₃): δ=7.13 (s, 2H), 7.05 (s, 2H), 6.93 (s, 2H), 6.09 (m, 2H), 5.45 (d, J=18.81 Hz, 2H), 5.30 (d, J=10.45 Hz, 2H), 4.59 (m, 8H), 3.78-3.59 (m, 65H), 3.55 (m, 2H), 3.39 (s, 3H).

Example 2g: Compound 14, 5,5'-bis[ω-methyl-(ethyleneoxy)$_{12-20}$ methyl]-3,3'-bis[(prop-3-triethoxysilyl-1-yl)oxy]-1,1'-biphenyl To a solution of 13 (222.3 mg, 0.124 mmol) and triethoxysilane (84.8 mg, 95.3 μL, 0.497 mmol, 4.0 eq) in toluene (1.5 ml), Karstedt's catalyst (16.6 μl, 2.1-2.3 mol % in xylene) was added and the resulting solution heated up to 40° C. overnight. The reaction was monitored by $^1$H NMR following the disappearance of the olefinic protons and the appearance of the triethoxysilyl group in the molecule. The resulting orange solution was cooled down to room temperature and the solvent evaporated under reduced pressure. To remove the residual traces of unreacted triethoxysilane, toluene (3.0 ml×3) was added and evaporated again under reduced pressure to obtain 14 (262.6 mg) as an orange oil (99% yield) which was used directly for coating experiments.

Example 3: Synthesis of Compound 20, 1,3-bis[ω-methyl-(ethyleneoxy)$_{12-20}$methyl]-4,6-bis[(prop-3-triethoxysilyl-1-yl)oxy]benzene

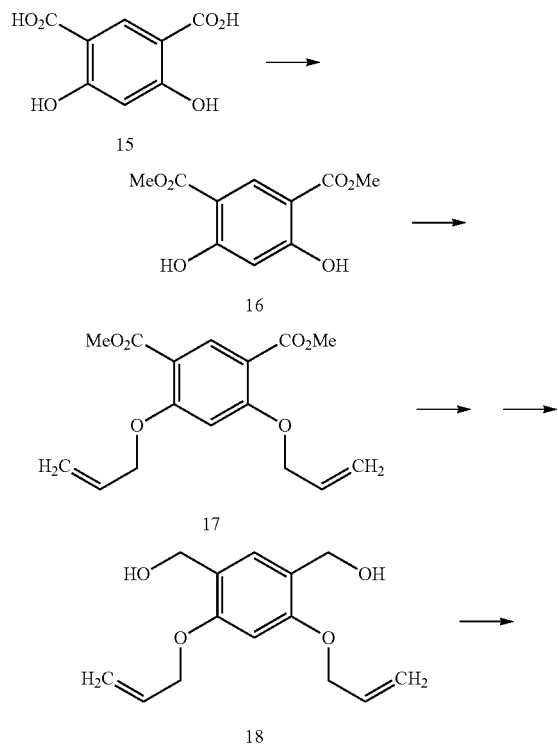

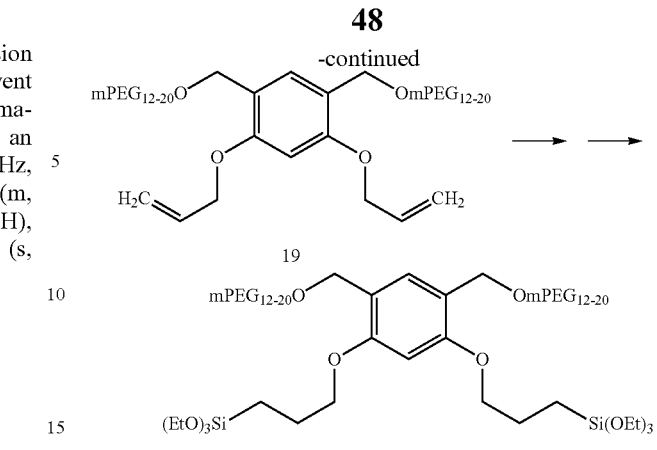

Example 3a: Compound 16, 4,6-dihydroxy Isophtalic Acid Dimethyl Ester

To a solution of 15 (700.0 mg, 3.36 mmol) in MeOH (18 ml), SOCl₂ (1.63 g, 1.22 ml, 13.43 mmol, 4.0 eq) was added dropwise at 0° C. When the addition was completed the reaction mixture was refluxed overnight. The resulting suspension was cooled down to 0° C. and then filtered, washing with cold methanol, to obtain 16 as white crystals (506.2 mg, 2.24 mmol, 67% yield). $^1$H and $^{13}$C NMR in agreement with literature reference [*Eur. J. Org. Chem.* 2013, 36, 8135-8144].

Example 3b: Compound 17, 4,6-diallyloxy Isophtalic Acid Dimethyl Ester

The same procedure as for synthesizing 11 was applied for the synthesis of compound 17. Yield=79%. $^1$H NMR (400 MHz, CDCl₃): δ=8.49 (s, 1H), 6.49 (s, 1H), 6.12-6.02 (m, 2H), 5.56 (d, J=17.33 Hz, 2H), 5.36 (d, J=10.61 Hz, 2H), 4.68 (d, J=4.77 Hz, 4H), 3.88 (s, 6H).

Example 3c: Compound 18, 1,3-bis(hydroxymethyl)-4,6-diallyloxy Benzene

The same procedure as for synthesizing 12 was applied for the synthesis of compound 18. Yield=99%. $^1$H NMR (400 MHz, CDCl₃): δ=7.20 (s, 1H), 6.47 (s, 1H), 6.11-6.01 (m, 2H), 5.42 (d, J=17.15 Hz, 2H), 5.31 (d, J=10.61 Hz, 2H), 4.64 (s, 4H), 4.58 (d, J=5.13 Hz, 4H).

Example 3d: Compound 19, 1,3-bis[ω-methyl(ethyleneoxy)$_{12-20}$methyl]-4,6-[(prop-2-en-1-yl)oxy] benzene To a solution of the diol 18 (50.0 mg, 0.20 mmol) in DCM (3.0 ml), PBr₃ (0.499 ml, 1 M in DCM, 0.50 mmol, 2.5 eq) was added at 0° C. After 20 minutes, a solution of saturated NaHCO₃ was added and the organic layer separated. The water phase was extracted with DCM (3×3 ml) and the combined organic phases were dried over MgSO₄, filtrated, and the solvent evaporated under reduced pressure to give the dibrominated intermediate as a yellow solid. In another Schlenk flask, charged with a solution of m-PEG$_{12-20}$-OH (327.1 mg, 0.43 mmol) in dioxane (0.5 ml), NaH (21.6 mg, 0.54 mmol, 60% dispersion in mineral oil) was added at 12° C. and the resulting suspension stirred for 30 minutes after which a solution of the previously prepared brominated intermediate in dioxane (0.5 ml) was added at the same temperature. The reaction mixture was then allowed to warm up to room temperature and stirred for 40 h. The suspension was then quenched with H$_2$O (0.1 ml) and the solvent evaporated. The resulting oil was purified by flash chromatography (DCM→DCM:MeOH=96:4) to get 19 (301.1 mg, 0.176 mmol, 89% yield) as a yellowish oil. $^1$H NMR (400 MHz, CDCl$_3$): δ=7.32 (s, 1H), 6.42 (s, 1H), 6.04 (m, 2H), 5.41 (d, J=16.71 Hz, 2H), 5.27 (d, J=10.59 Hz, 2H), 4.54 (m, 6H), 3.75-3.58 (m, 60H), 3.55 (m, 2H), 3.38 (s, 3H).

Example 3e: Compound 20, 1,3-bis[ω-methyl-(ethyleneoxy)$_{12-20}$methyl]-4,6-bis[(prop-3-triethoxysilyl-1-yl)oxy]benzene The same procedure as for synthesizing 14 was applied for the synthesis of compound 20 (yield=99%) which was used directly for coating experiments.

Example 4: Synthesis of Compound 26, 1-(ω-methyl-(ethyleneoxy)$_{12-20}$methyl)-3,5-bis[(but-4-triethoxysilyl-1-yl)oxy]benzene

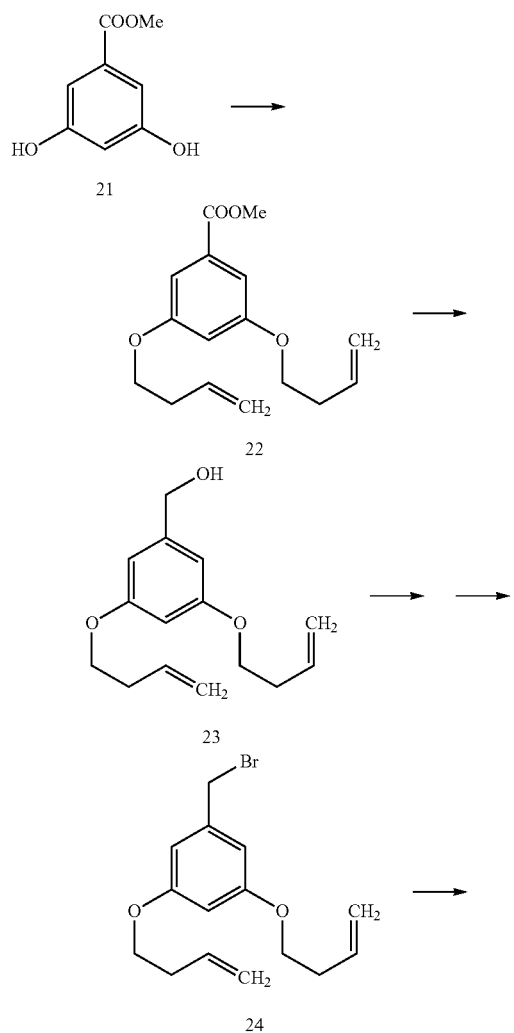

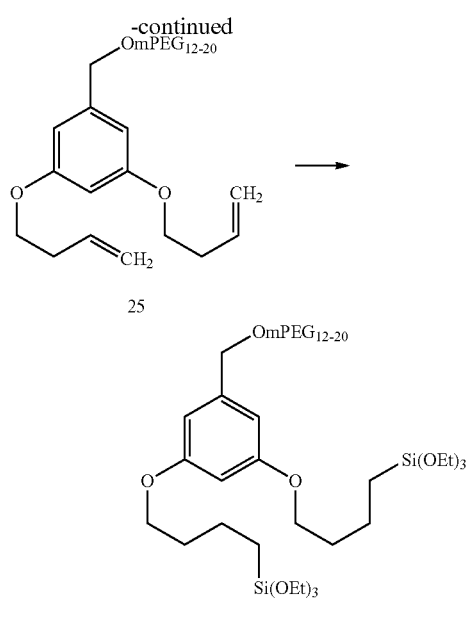

Example 4a: Compound 22, 3,5-bis[(but-3-en-1-yl)oxy]benzoic Acid Methyl Ester

The same procedure as for synthesizing 11 was applied for the synthesis of compound 21. Yield=78%. $^1$H NMR (400 MHz, CDCl$_3$): δ=7.18 (d, J=2.48 Hz, 2H) 6.66 (t, J=2.30 Hz, 1H), 5.96-5.85 (m, 2H), 5.18 (dq, J=17.15, 1.59 Hz, 2H), 5.12 (dq, J=10.26, 1.24 Hz, 2H), 4.04 (t, J=6.72 Hz, 4H), 3.91 (s, 3H), 2.55 (tq, J=6.72, 1.41 Hz, 4H).

Example 4b: Compound 23, 3,5-bis[(but-3-en-1-yl)oxy]benzyl Alcohol

To a solution of 22 (250.0 mg, 0.91 mmol) in THF (4 ml), LAH (72.3 mg, 1.81 mmol, 2.0 eq) was added at 0° C. under nitrogen atmosphere. The reaction was monitored by TLC until the complete conversion of 22 to 23, then it was stirred for an additional hour and quenched according to the Fieser work up (*J. Org. Chem.* 1953, 18, 1190). The collected filtrate was passed through a short silica pad (heptane:EtOAc=2:1, R$_f$=0.35) to obtain 23 (208.0 mg, 0.84 mmol, 93% yield) as a colorless oil, which was used in the next step.

Example 4c: Compound 24, 3,5-bis[(but-3-en-1-yl)oxy]benzyl Bromide

To a solution of 23 (208.0 mg, 0.20 mmol) in DCM (3.0 ml), PBr$_3$ (0.499 ml, 1 M in DCM, 0.50 mmol, 2.5 eq) was added at 0° C. After 20 minutes a solution of sat. NaHCO$_3$ was added and the organic layer separated. The water phase was extracted with DCM (3×3 ml) and the collected organic phase was dried over MgSO$_4$, filtrated and the solvent evaporated under reduced pressure. The resulting orange oil was passed through a short silica pad (heptane:EtOAc=2:1) to obtain 24 (120.7 mg, 0.39 mmol, 46% yield) as a colorless oil. $^1$H NMR (400 MHz, CDCl$_3$): δ=6.54 (d, J=2.12 Hz, 2H), 6.40 (t, J=2.30 Hz, 1H), 5.96-5.84 (m, 2H), 5.18 (dd, J=17.15, 1.41 Hz, 2H), 5.12 (dd, J=10.26, 1.24 Hz, 2H), 4.41 (s, 2H), 4.00 (t, J=6.72 Hz, 4H), 2.54 (q, J=6.54 Hz, 4H).

Example 4c: Compound 25, 1-[ω-methyl-(ethyleneoxy)$_{12-20}$methyl]-3,5-bis[(but-3-en-1-yl)oxy]benzene In a Schlenk flask to a solution of m-PEG$_{12-20}$-OH (364.0 mg, 0.43 mmol) in dioxane (0.5 ml), NaH (21.6 mg, 0.54 mmol) was added at 0° C. and the resulting suspension stirred for 30 minutes after which a solution of the previously prepared brominated intermediate 24 in dioxane (0.5 ml) was added at the same temperature. The reaction mixture was then allowed to warm up to room temperature and stirred for 40 h. The suspension was then quenched with H$_2$O (0.1 ml) and the solvent evaporated. The resulting oil was purified by flash chromatography (DCM→DCM:MeOH=96:4) to get 25 (301.1 mg, 0.176 mmol, 89% yield) as a yellowish oil. $^1$H NMR (400 MHz, CDCl$_3$): δ=6.50 (s, 2H), 6.38 (s, 1H), 5.90 (m, 2H), 5.17 (d, J=17.15 Hz, 2H), 5.10 (d, J=10.33 Hz, 2H), 4.49 (s, 2H), 3.99 (t, J=5.94 Hz, 4H), 3.72-3.59 (m, 53H), 3.55 (m, 2H), 3.38 (s, 3H), 2.53 (q, J=7.03 Hz, 4H).

Example 4d: Compound 26, 1-[ω-methyl-(ethyleneoxy)$_{12-20}$ methyl]-3,5-bis[(but-4-triethoxysilyl-1-yl)oxy]benzene The same procedure as for synthesizing 14 was applied for the synthesis of compound 26 (99% yield), which was used directly for coating experiments.

Example 5: Synthesis of Compound 33, 1-[ω-methyl-(ethyleneoxy)$_{12-20}$ methyl]-3,5-bis(eth-2-triethoxysilyl-1-yl)benzene

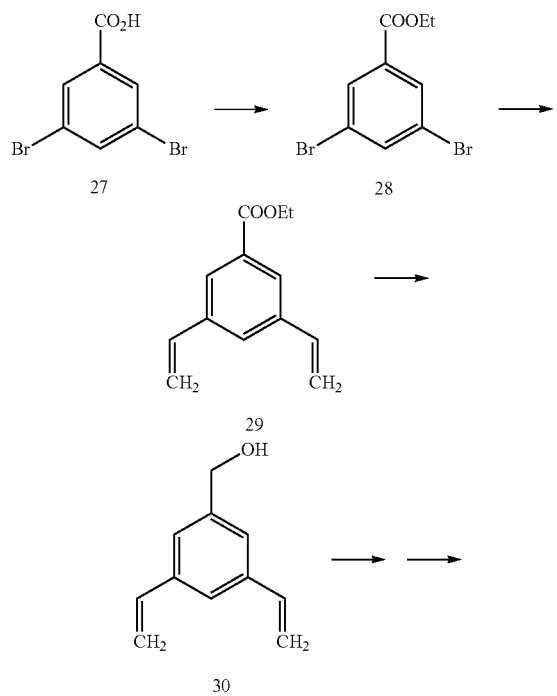

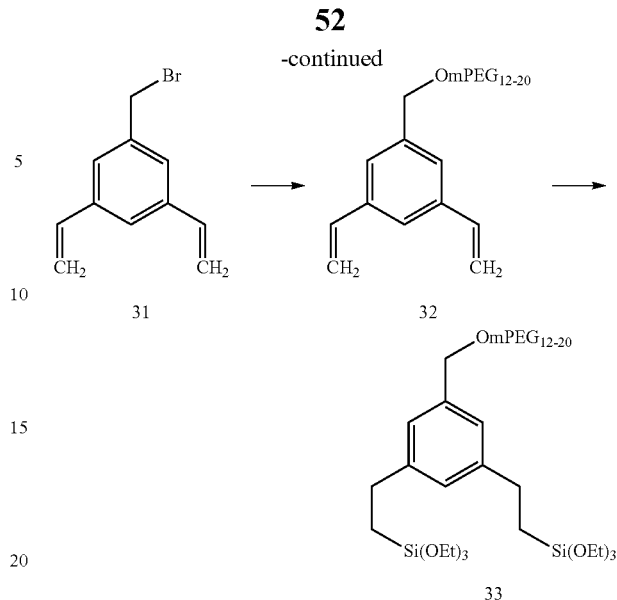

Example 5a: Compound 28, 3,5-dibromobenzoic Acid Ethyl Ester

The same procedure as for synthesizing 8 was applied for the synthesis of compound 28. Yield=90%. $^1$H and $^{13}$CNMR in agreement with literature reference (*Eur. J. Org. Chem.* 2009, 18, 2953-2955).

Example 5b: Compound 29, 3,5-divinylbenzoic Acid Ethyl Ester

In a flame dried Schlenk flask, to a solution of 28 (1.50 g, 4.87 mmol) and (Ph$_3$P)$_4$Pd (142.1 mg, 0.12 mmol, 0.03 eq) in toluene (15 ml), tributyl-vinyltin (3.90 g, 3.60 ml, 11.69 mmol, 2.4 eq) was added at room temperature under nitrogen atmosphere. The resulting reaction mixture was heated up to 80° C. overnight. The reaction mixture was then washed with brine and then stirred with a 10% NaF solution for 2 h. Phases were separated and the water phase was extracted with Et$_2$O (3×25 ml). The yellow oil obtained was purified by flash chromatography (heptane:EtOAc=50:1) to yield 29 (985.1 g, 3.79 mmol, 78% yield) as a colorless oil. $^1$H NMR (400 MHz, CDCl$_3$): δ=7.98 (d, J=1.77 Hz, 2H), 7.61 (t, J=1.77 Hz, 1H), 6.76 (dd, J=17.50, 10.96 Hz, 2H), 5.85 (dd, J=17.68, 0.53 Hz, 2H), 5.35 (d, J=10.96 Hz, 2H), 4.41 (q, J=7.25 Hz, 2H), 1.42 (t, J=7.25 Hz, 3H).

Example 5c: Compound 30, 3,5-divinylbenzylalcohol

The same procedure as for synthesizing 23 was applied to the synthesis of compound 30. Yield=93%. $^1$H NMR (400 MHz, CDCl$_3$): δ=7.37 (s, 1H), 7.33 (s, 2H), 6.73 (dd, J=17.51, 10.79 Hz, 2H), 5.80 (d, J=17.50 Hz, 2H), 6.29 (d, J=10.96 Hz, 2H), 4.71 (s, 2H).

Example 5d: Compound 31, 3,5-divinylbenzylbromide

The same procedure as for synthesizing 24 was applied for the synthesis of compound 31. Yield=42%. $^1$H NMR (400 MHz, CDCl$_3$): δ=7.37 (s, 1H), 7.34 (s, 2H), 6.71 (dd, J=17.68, 10.96 Hz, 2H), 5.80 (d, J=17.50 Hz, 2H), 6.32 (d, J=10.79 Hz, 2H), 4.50 (s, 2H).

Example 5e: Compound 32, 1-[ω-methyl-(ethyleneoxy)$_{12-20}$ methyl]-3,5-divinylbenzene The same procedure as for synthesizing 25 was applied for the synthesis of compound 32. Yield=68%. $^1$H NMR (400 MHz, CDCl$_3$): δ=7.35 (s, 1H), 7.30 (s, 2H), 6.72 (dd, J=18.48, 11.55 Hz, 2H), 5.78 (d, J=17.51 Hz, 2H), 5.27 (d, J=10.91 Hz, 2H), 4.57 (s, 2H), 3.72-3.61 (m, 59H), 3.56 (m, 2H), 3.39 (s, 3H).

Example 5f: Compound 33, 1-[ω-methyl-(ethyleneoxy)$_{12-20}$ methyl]-3,5-bis(eth-2-triethoxysilyl-1-yl) benzene The same procedure as for synthesizing 14 was applied for the synthesis of compound 33 (99% yield), which was used directly for coating experiments.

Example 6: Synthesis of Compound 38, 1-[ω-methyl-(ethyleneoxy)$_{12-20}$ methyl]-3,5-bis(prop-3-triethoxysilyl-1-yl)benzene

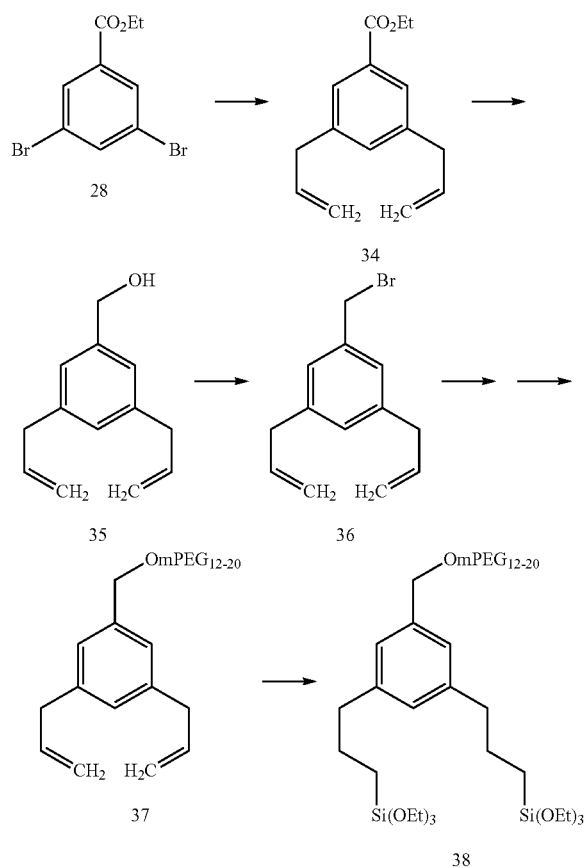

Example 6a: Compound 34, 3,5-diallylbenzoic Acid Ethyl Ester

The same procedure as for synthesizing 29 was applied for the synthesis of compound 34 but allyltributyltin was used instead of tributyl-vinyltin. Yield=73%. $^1$H NMR (400 MHz, CDCl$_3$): δ=7.73 (s, 2H), 7.21 (s, 1H), 6.02-5.92 (m, 2H), 5.10 (d, J=13.44 Hz, 4H), 4.38 (q, J=7.07 Hz, 2H), 3.42 (d, J=6.72 Hz, 4H), 1.40 (t, J=7.07 Hz, 3H).

Example 6b: Compound 35, 3,5-diallylbenzylalcohol

The same procedure as for synthesizing 23 was applied for the synthesis of compound 35 (98% yield), which was used directly in the next step.

Example 6c: Compound 36, 3,5-diallylbenzylbromide

The same procedure as for synthesizing 24 was applied for the synthesis of compound 36. Yield=58%. $^1$H NMR (400 MHz, CDCl$_3$): δ=7.08 (s, 2H), 6.97 (s, 1H), 6.02-5.92 (m, 2H), 5.11 (m, 4H), 4.47 (s, 2H), 3.38 (d, J=6.72 Hz, 4H).

Example 6d: Compound 37, 1-[ω-methyl-(ethyleneoxy)$_{12-20}$ methyl]-3,5-diallylbenzene The same procedure as for synthesizing 25 was applied for the synthesis of compound 37. Yield=68%. $^1$H NMR (400 MHz, CDCl$_3$): δ=7.00 (s, 2H), 6.92 (s, 2H), 5.94 (m, 2H), 5.06 (m, 4H), 4.50 (s, 2H), 3.75-3.57 (m, 50H), 3.54 (m, 2H), 3.36 (m, 5H).

Example 6e: Compound 38, 1-[ω-methyl-(ethyleneoxy)$_{12-20}$ methyl]-3,5-bis(prop-3-triethoxysilyl-1-yl) benzene The same procedure as for synthesizing 14 was applied for the synthesis of compound 38 (99% yield), which was used directly for coating experiments.

Example 7: Synthesis of Compound 41, 1,7-bis(triethoxysilyl)-4-(prop-3-triethoxysilyl-1-yl)-4-[ω-methyl-(ethyleneoxy)$_{12-20}$]heptane

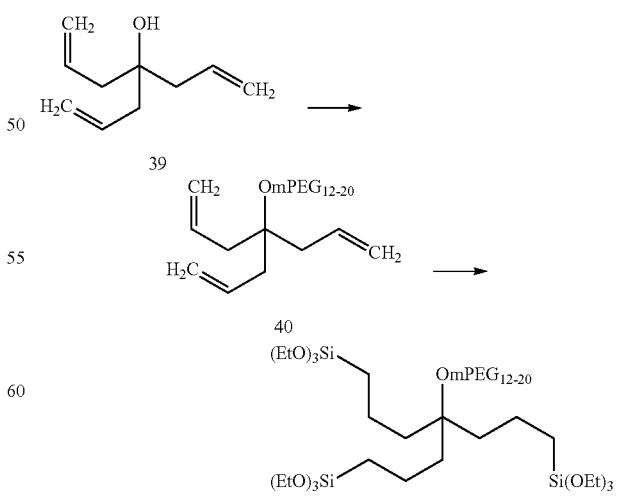

Example 7a: Compound 40, 4-allyl-4-[ω-methyl-(ethyleneoxy)$_{12-20}$]hepta-1,6-diene The same procedure as for synthesizing 13 was applied for the synthesis of compound 40, using 0.6 eq instead of 1.9 eq of 56 and DMF as solvent. Yield=30%. $^1$H NMR (400 MHz, CDCl$_3$): δ=5.81 (m, 3H), 5.06 (m, 6H), 3.72-3.52 (m, 66H), 3.38 (s, 3H), 2.25 (d, J=7.24 Hz, 6H).

Example 7b: Compound 41, 1,7-bis(triethoxysilyl)-4-(prop-3-triethoxysilyl-1-yl)-4-[ω-methyl-(ethyleneoxy)$_{12-20}$]heptane The same procedure as for synthesizing 14 was applied for the synthesis of compound 41 (99% yield), which was used directly for coating experiments.

Example 8: Synthesis of Compound 44, 1,7-bis(triethoxysilyl)-4-[ω-methyl-(ethyleneoxy)$_{12-20}$]heptane

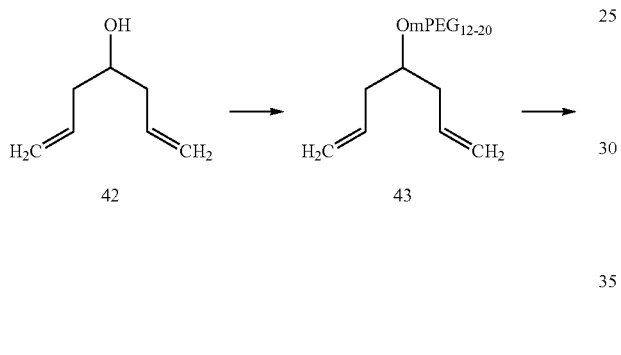

Example 8a: Compound 43, 4-[ω-methyl-(ethyleneoxy)$_{12-20}$]hepta-1,6-diene The same procedure as for synthesizing 40 was applied for the synthesis of compound 43. Yield=45%. $^1$H NMR (400 MHz, CDCl$_3$): δ=5.82 (m, 2H), 5.05 (m, 4H), 3.75-3.57 (m, 64H), 3.55 (m, 2H), 3.38 (s, 3H), 2.26 (t, J=5.53 Hz, 4H).

Example 8b: Compound 44, 1,7-bis(triethoxysilyl)-4-[ω-methyl-(ethyleneoxy)$_{2-20}$]heptane The same procedure as for synthesizing 14 was applied for the synthesis of compound 44, (99% yield), which was used directly for coating experiments.

Example 9, Synthesis of Compound 49, 1-[ω-methyl-(ethyleneoxy)$_{12-20}$ methyl]-2,4-bis(eth-2-triethoxysilyl-1-yl)cyclopentane

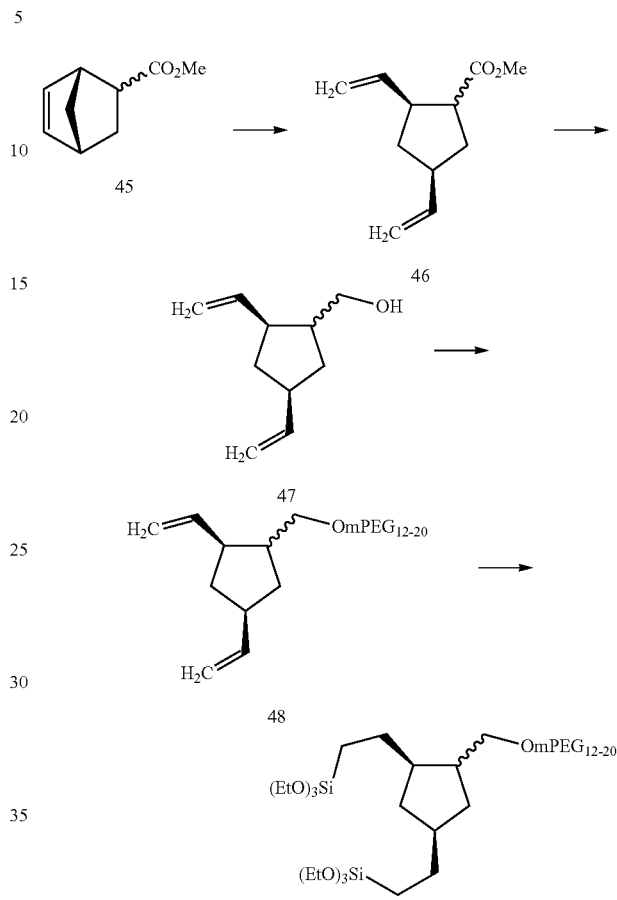

Example 9a: Compound 46, 2,4-divinylcyclopentane carboxylic acid methyl ester In a flame dried Schlenk flask, to a solution of methyl 5-norbornene-2-carboxylate (45) (1.06 g, 1.00 ml, 6.69 mmol) in degassed DCM (150 ml), a solution of benzylidene-bis(tricyclohexylphosphine)dichlororuthenium (170.0 mg, 0.20 mmol, 0.03 eq) in degassed DCM (3 ml) was added. The flask was then evacuated and backfilled with ethylene (3 times) and the resulting solution stirred overnight at room temperature. The solvent was then evaporated under reduced pressure and the crude dark oil purified by flash chromatography (heptane:EtOAc=9:1) to obtain 46 (840.2 mg, 4.66 mmol, 70%) as a mixture of diastereoisomers, as a dark oil. $^1$H NMR (mixture of diastereoisomers) (400 MHz, CDCl$_3$): δ=5.79 (m, 3.5H), 5.12-4.88 (m, 6.5H), 3.69 (s, 3H), 3.63 (s, 2H), 3.07-2.46 (m, 5H), 2.18-1.91 (m, 4H), 1.91-1.70 (m, 2H), 1.52 (m, 1H), 1.32 (m, 1H).

Example 9b: Compound 47, 1-hydroxymethyl-2,4-divinylcyclopentane

The same procedure as for synthesizing 23 was applied for the synthesis of compound 47. The reaction was monitored by TLC until the complete conversion of 46 ($R_f$=0.88, heptane:EtOAc=2:1) to 47 ($R_f$=0.49, heptane:EtOAc=2:1). Yield=89%.

Example 9c: Compound 48, 1-[ω-methyl-(ethyleneoxy)$_{12-20}$methyl]-2,4-divinylcyclopentane The same procedure for synthesizing 40 was applied for the synthesis of compound 48. The reaction was monitored by TLC until the complete conversion of 47 to 48 ($R_f$=0.29-0.59, DCM:MeOH=96:4). Yield=88%.

Example 9d: Compound 49, 1-[ω-methyl-(ethyleneoxy)$_{12-20}$methyl]-2,4-bis(eth-2-triethoxysilyl-1-yl)cyclopentane The same procedure for synthesizing 14 was applied for the synthesis of compound 49, (99% yield), which was used directly for coating experiments.

Example 10: Synthesis of Compound 51, 1-[ω-methyl-(ethyleneoxy)$_{9-12}$ methyl]-3,5-bis[(prop-3-triethoxysilyl-1-yl)oxy]benzene

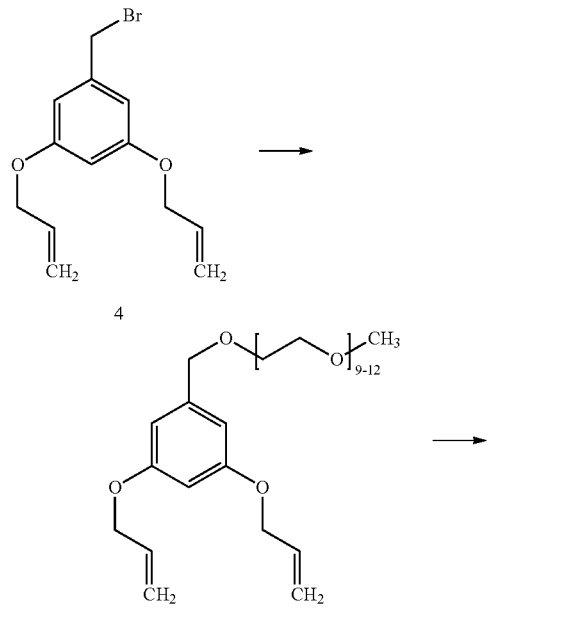

Example 10a: Compound 50, 1-[ω-methyl-(ethyleneoxy)$_{9-12}$methyl]-3,5-bis[(prop-2-en-1-yl)oxy]benzene The same procedure for synthesizing 29 was applied for the synthesis of compound 50. Yield=88%. $^1$H NMR (400 MHz, CDCl$_3$): δ=6.52 (s, 2H), 6.42 (s, 1H), 6.05 (m, 2H), 5.41 (d, J=17.17 Hz, 2H), 5.28 (d, J=10.81 Hz, 2H), 4.51 (m, 6H), 3.75-3.59 (m, 40H), 3.55 (m, 2H), 3.39 (s, 3H).

Example 10b: Compound 51, 1-[ω-methyl-(ethyleneoxy)$_{9-12}$methyl]-3,5-bis[(prop-3-triethoxysilyl-1-yl)oxy]benzene The same procedure as for synthesizing 14 was applied for the synthesis of compound 51, (99% yield), which was used directly for coating experiments.

Example 11: Synthesis of Compound 54, N,N-bis(prop-3-trimethoxysilyl-1-yl)-2-[ω-methyl-(ethyleneoxy)$_{8-11}$]acetamide

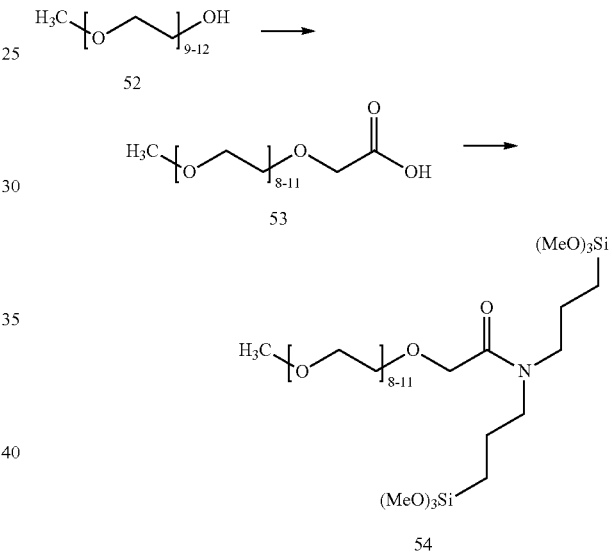

Example 11a: Compound 53, 2-[ω-methyl-(ethyleneoxy)$_{8-11}$]acetic Acid

Compound 52 (5 g, 10 mmol) was dissolved in 1 M aqueous NaOH. A solution of potassium permanganate (3.48 g in 110 ml H$_2$O) was added dropwise. After complete addition the reaction mixture was left to stir overnight. The manganese oxide was filtered off and the pH of the clear solution was adjusted to 4 by the addition of 1 M aqueous HCl. The water was evaporated and two small portions of toluene was added and evaporated to drive off the moisture. The product was dissolved/suspended in DCM (100 ml), filtered and evaporated to dryness. Yield 3.8 g, 75%. $^1$H NMR (400 MHz, CDCl$_3$): δ=4.19 (s, 2H), 3.67 (m, 33H), 3.39 (s, 3H).

Example 11b: Compound 54, N,N-bis(prop-3-trimethoxysilyl-1-yl)-2-[ω-methyl-(ethyleneoxy)$_{8-11}$-]acetamide A solution of compound 53 (3.8 g, 7.5 mmol) and carbonyldiimidazole (1.22 g, 7.5 mmol) in THF (50 ml) was refluxed for two hours. The reaction mixture was allowed to cool and then bis(3-trimethoxysilylprop-1-yl)amine (2.27 ml, 2.36 g, 7 mmol) was added and it was then left to stir overnight. The solvent was evaporated and NMR revealed the desired product 54 plus the expected free imidazole. The mixture was used directly to coat nanostructures analogously to example 12b.

Example 12: a) Synthesis of Uncoated Nanostructures by the Polymerization of 1,1-bis(prop-3-trimethoxysilyl-1-yl)-1,1-bis(dimethylphosphonato) methane A 5 l reactor with a PTFE coated stirrer was filled with nitrogen by three vacuum/nitrogen cycles and sterilized by setting the jacket temperature to 130° C. for 2 h. The jacket temperature was set to 25 degrees and ethyleneglycol (4 l) and 1,1-bis(3-triethoxysilylprop-1-yl)-1,1-bis(dimethylphosphonato)methane (165 g, 257 mmol, Mw=640.8 g/mol) were added. Then water (1.0 l) was added during stirring. The reaction mixture was degassed by three vacuum/nitrogen cycles. The temperature was ramped up to 137° C. during 2 h, kept at 137° C. for 6 h and then ramped down to 25° C. again during 2 h. The reaction mixture was refluxing with an inner temperature of 123° C. A peristaltic pump was used to circulate the reaction solution through an in line filter (0.2 μm cut-off) for 3 h to make the reaction mixture clear. To characterize the uncoated nanostructures a sample was taken out and washed free from solvent residues by repeated dilution-filtration cycles on a 10 kDa spinfilter.

b) Coating with 1-[ω-methyl-(ethyleneoxy)$_{12-20}$ methyl]-3,5-bis[(prop-3-triethoxysilyl-1-yl)oxy]benzene To the reaction mixture of example 12a was added urea (155 g) and the jacket temperature was set to 92° C. Compound 6 of example 1 (98 g, 76 mmol, Mw=1283 g/mol) was added dropwise over 10 h by a syringe pump. In a 50 ml flask MnCl$_2$.4H$_2$O (7.84 g, 39.6 mmol, Fw=197.84) was dissolved in water (25 ml). This solution was added to the reactor in one portion. The jacket temperature was increased to 105° C. and kept there for 96 h.

c) Filtration

The coated nanostructure of example 12b was first passed through an in-line filter (0.2 μm cut-off) to produce a clear solution. The pre-filtered solution was then diluted 20× with either 0.9% NaCl (aq) or Milli-Q water. Ultrafiltration was followed using a tangential flow filter with cut-off of 50 kDa or 100 kDa (Pall Centramate T-Series cassette or Sartorius Vivaflow 200) and collected on a 10 kDa cassette (Pall Centramate T-series cassette or Sartorius Vivaflow 200). Diafiltration using 10 kDa filter involved addition of Milli-Q water (10× the volume of the coated nanostructure solution) to exchange the nanostructure solution solvent with water.

d) Characterization

The following physical and chemical properties of purified nanostructure solution was analyzed: (i) Chemical composition using ICP-OES; A typical composition is P/Mn=7.6 and Si/P=1.4 (ii) Size distribution using GPC and DLS; A typical value is 5 nm (iii) Stability against EDTA—by adding equivalent amount of EDTA to the Mn-amount present in the nanostructure followed by subjecting to 10 kDa filtration and collecting and analyzing the filtrate's composition via ICP-OES, a typical stability value is 20% of EDTA(iv) Relaxivity (n) of the nanostructure in water using the Bruker minispec at 1.5 T and 37° C. A typical value is 13.5/s/mM Mn.

The coating density $N_{coat}/A_{core}$, where $N_{coat}$ is the number of moles of coating molecules attached to the nanostructure and $A_{core}$ is the area of the uncoated nanostructure, is calculated according to the formula:

$$\frac{N_{coat}}{A_{core}} = \frac{(B-A)d_{core}\rho_{core}}{6M_{monomer}}$$

where $d_{core}$ is the hydrodynamic diameter of the uncoated nanostructures of Example 12a as measured by DLS, $\rho_{core}$ is the measured density of the core (1.7 g/ml=1.7×10$^6$ g/m$^3$), A is the measured (by ICP-OES) Si/P ratio of the core nanostructures, B is the measured (by ICP-OES) Si/P ratio of the coated nanostructures and $M_{monomer}$ is the molecular weight of the monomer after polymerization and partial hydrolysis. Elemental analysis of a dried sample of the core suggests a composition of C$_8$H$_{20}$O$_9$P$_2$Si$_2$ with a molecular weight of the monomer residues of 378 g/mol. For the current example A was measured to be 1.0 and B to be 1.67 so the coating density is calculated to be (1.67-1.0)×5×10$^{-9}$ m×1.7×10$^6$ g/m$^3$/(6×378 g/mol)=2.5×10$^{-6}$ mol/m$^2$ or 1.6 coating molecules/nm$^2$.

Example 13: Synthesis of Nanostructures Coated with a) 1-[ω-methyl-(ethyleneoxy)$_{9-12}$ methyl]-3,5-bis(prop-3-triethoxysilyl-1-yl)oxy]benzene, b) N,N-bis(prop-3-trimethoxysilyl-1-yl)-2-[ω-methyl-(ethyleneoxy)$_{8-11}$]acetamide a) In a similar fashion as Example 11 but with compound 6 changed to compound 51, nanostructures coated with 1-[ω-methyl-(ethyleneoxy)$_{9-12}$ methyl]-3,5-bis[(prop-3-triethoxysilyl-1-yl)oxy]benzene, were synthesized.

b) In a similar fashion as Example 11 but with compound 6 changed to compound 54, nanostructures coated with N,N-bis(prop-3-trimethoxysilyl-1-yl)-2-[ω-methyl-(ethyleneoxy)$_{8-11}$]acetamide were synthesized.

Example 14: Synthesis and Characterization of Nanostructures Coated with a Series of Silanes A small amount of uncoated nanostructures similar to those of example 12a was prepared by mixing 1.15 g 1,1-bis(prop-3-triethoxysilyl-1-yl)-1,1-bis(dimethylphosphonato)methane, ethyleneglycol (25.5 ml), water (8 ml), and a solution of MnCl$_2$.4H$_2$O (2.77 ml of a solution of 890 mg MnCl$_2$.4H$_2$O in 2.9 ml ethyleneglycol) in a vial. The vial was sealed and heated to 92° C. for 24 h.

To a series of 4 ml vials was added 0.1 mmol, respectively, of the coating precursors of table 1, dissolved in 0.8 ml ethyleneglycol and 2 ml of the above solution of uncoated nanostructures. The vials were flushed with nitrogen, sealed and heated in a heater/shaker for 20 h.

TABLE 1

Summary of results for a series of coated nanomaterials.

| Coating precursor | Soluble product | Loss of coating | Ca resistance |
|---|---|---|---|
| A | Y | 5% | Y |
| 6 | Y | 0 | Y |
| 14 | Y | 0 | Y |
| 20 | N | nt | nt |
| 26 | Y | 0 | nt |
| 33 | Y | 0 | nt |
| 41 | N | nt | nt |
| 38 | partial | 1% | nt |
| 43 | Y | 0 | Y |

A = 1-[ω-methyl-(ethyleneoxy)$_{12-20}$]-3-(prop-3-triethoxysilyl-1-yl-,
"Loss of coating" according to the method in example 17,
"Ca resistance" according to the method of example 15,
nt = not tested.

Example 15. Calcium Induced Aggregation of the Coated Nanostructrues

Volumes of nanostructure were added to 1 ml aliquots of 10 mM Tris-HCl 150 mM NaCl pH 7.4 containing 0, 0.5, 1, 2, 4 and 8 mM CaCl$_2$) in microcentrifuge tubes so that the final concentration of phosphorus was 0.5 mM. The samples were vortexed, incubated at room temperature for 1 h and centrifuged for 10 min at 12000×g. The supernatants (700 µl) were removed and analyzed by ICP for phosphorus concentrations. The phosphorus concentrations were normalized to the concentration in corresponding samples without CaCl$_2$) and plotted as '% remaining in solution' against the concentration of CaCl$_2$) in the reaction mixture. When 90% or more remains in solution the material is considered robust against calcium induced aggregation.

Example 16: Synthesis of Compound 56, m-PEG$_{12-20}$-OMs

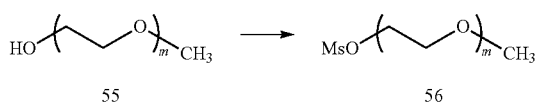

In a three necked bottom flask, to a solution of m-PEG$_{12-20}$-OH (55) (5.0 g, 6.47 mmol), diisopropylethylamine (1.71 mL, 1.27 g, 9.70 mmol, 1.5 eq) in DCM (65 mL), mesyl chloride (0.61 mL, 0.91 g, 7.76 mmol, 1.2 eq) was added dropwise at 0° C. The mixture was allowed to warm up to room temperature and stirred overnight. Then diethyl ether (50 mL) was added and the precipitate filtered off. The filtrate was evaporated to get a yellow oil which was purified by flash chromatography (DCM: MeOH=15:1) to obtain 56 (4.51 g, 5.45 mmol, 84% yield) as a colorless oil.

Example 17: Heat Treatment

The sample was moved to a 20 mL flask and degassed by three N$_2$-vacuum cycles and was then kept under N$_2$. The sample was heated in a silicon oil bath at 80° C. for 30 minutes and was then cooled to ambient room temperature. A reference aliquot was withdrawn (A). The remaining sample was washed with four times with milliQ water on a 10 kDa Vivaspin 6 centrifugation filter (Sartorious). A reference aliquot (B) was withdrawn from the retentate. Reference aliquots A, and B were analyzed with ICP-OES. A stable sample shows unchanged Si/P ratio in aliquot B compared to aliquot A, and a sample that loses coating will have a lower Si/P ratio.

Figure 3:
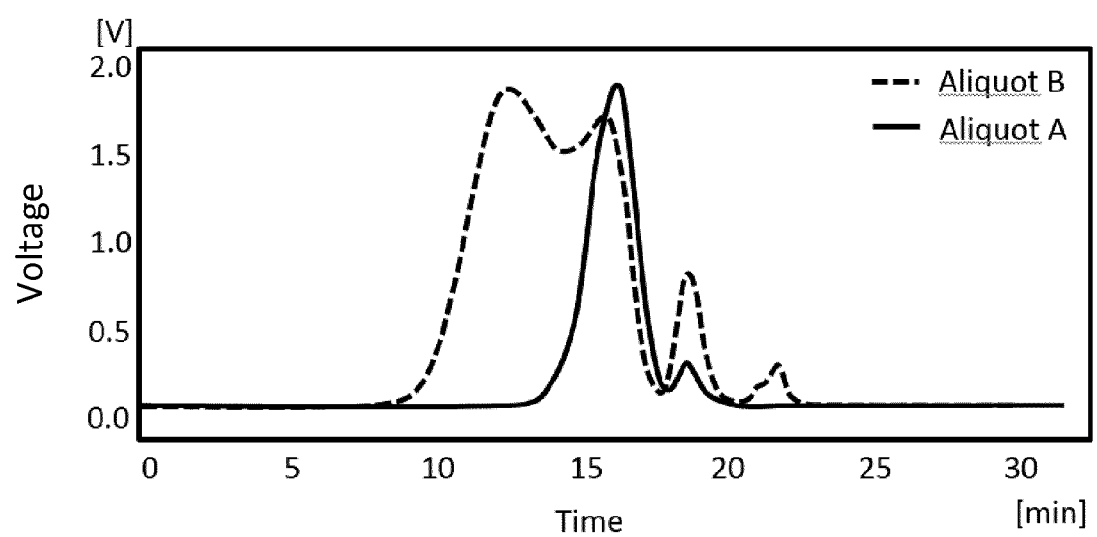
FIG. 3 shows the results of gel filtration chromatography (GFC) of two aliquots, A and B, taken during manganese loading of nanostructures coated with N,N-bis(3-trimethoxysilylprop-1-yl)-2-[ω-methyl-(ethyleneoxy)$_{8-11}$]acetamide (Example 18 below).

Example 18: Manganese Loading of Nanostructures Coated with N,N-bis(3-trimethoxysilylprop-1-yl)-2-[ω-methyl-(ethyleneoxy)$_{8-11}$]acetamide 200 ml of the crude solution of coated nanostructures of Example 13b was added a solution of 0.256 g MnCl$_2$.4H$_2$O dissolved in 2.56 ml ethylene glycol. The pH was adjusted to 4.07 with 1 M NaOH. The manganese solution was added to the reaction. An aliquot A was taken out. The reaction was heated at 100° C. for 25 h 30 min after which the temperature descended to ambient room temperature. An aliquot B was withdrawn. Aliquots A and B were analyzed with GFC (see FIG. 3) which showed that loading the coated nanostructures with manganese (aliquot B) resulted in a drastic decrease in retention time which corresponds to an increased nanomaterial size due to aggregation.

Example 19 Test of a Series of Additives for the Coating Process

Nanostructure cores were synthesized as described in the first part of example 14. Aliquots of 4 ml of this solution was added to a series of six vials. They were flushed with nitrogen and placed in a heater shaker at 90° C. To each vial was added additive according to table 2 and then 26 mg of compound 6, every two hours, three times, in total 78 mg to each. After 12 h 1 mL of a 26.7 mM solution of MnCl$_2$ in ethylene glycol:water, 80:20. The vials were heated to 100° C. for 5 days. The samples were filtered through a 50 kDa spinfilter and then collected on a 10 kDa spinfilter and washed with 5 portions of water and yield was determined by ICP analysis and Mn stability by measuring the relaxivity in the presence of increasing amounts of EDTA.

TABLE 2

Summary of the effect of different additives on the coating of nanostructures.

| Additive | Amount (mg) | Mn stability against EDTA | Yield, % after filtration |
|---|---|---|---|
| Urea | 120 | 18 | 60 |
| Ammonia, 25% | 137 | 21 | 78 |
| Formamide | 90 | 8 | 49 |
| N,N-dimethyl urea | 176 | 7 | 63 |
| Ammonium carbonate | 192 | 21 | 53 |
| Acetamide | 118 | 13 | 56 |
| none | — | 25 | 5 |

The invention claimed is:
1. A chemical compound comprising an aromatic core, or a carbocyclic, non-aromatic, core, wherein the aromatic core is a benzene ring or a biphenyl; the carbocyclic, non-aromatic core is a 5 to 7 membered ring; and
the core having covalently attached thereto:
at least two anchoring groups, each anchoring group comprising an activated silane group, wherein the anchoring groups have the following general formula -A-(CH$_2$)$_n$SiY$_3$ wherein A is a covalent bond or O, "n" is an integer from 1 to 3, and Y is independently a methoxy group or an ethoxy group; and at least one hydrophilic group extending from the core, the hydrophilic group comprising one or more hydrophilic polymer residues with a molecular composition of (aO+bN)/(cC+dS+eSi+fP)>0.3 where a, b, c, d, e and f are the mol percentage of oxygen (O), nitrogen (N), carbon (C), sulfur (S), silicon (Si) and phosphorus (P), respectively; wherein the hydrophilic polymer residue(s) is(are) selected, independently of each other if more than one hydrophilic group is present, from —(O—CH$_2$—CH$_2$)$_m$—OX, wherein X is CH$_3$ or H, and "m" is an integer from 6 to 25;

wherein the number of hydrophilic groups extending from the core is from one to the number of ring structures in the core.

2. The chemical compound according to claim 1, wherein the aromatic core is a benzene ring, having the general formula 1,

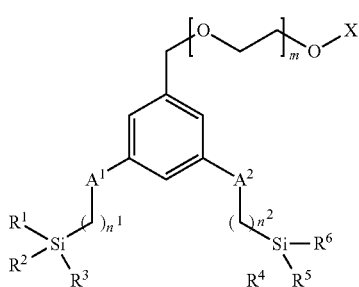

Formula 1 wherein

A$^1$ and A$^2$ are independently selected from the group consisting of a covalent bond or O;

"n$^1$" is an integer from 1 to 3;

"n$^2$" is an integer from 1 to 3;

R$^1$ to R$^6$ are independently selected from a methoxy group and an ethoxy group;

"m" is an integer from 6 to 25; and

X is methyl.

3. The chemical compound according to claim 2, wherein A$^1$ and A$^2$ are O, "n$^1$" is 3, "n$^2$" is 3, R$^1$ to R$^6$ are ethoxy, and X is methyl.

4. The chemical compound according to claim 1, wherein the aromatic core is a benzene ring, having the general formula 1,

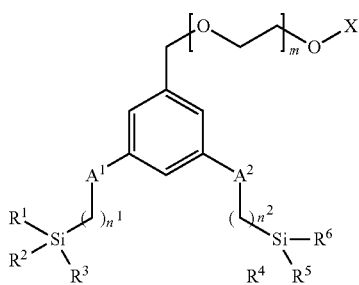

Formula 1 wherein

A$^1$ and A$^2$ are O;

"n$^1$" is 3;

"n$^2$" is 3;

R$^1$ to R$^6$ are independently selected from a methoxy group and an ethoxy group;

"m" is an integer from 12 to 20; and

X is methyl.

5. The chemical compound according to claim 1, wherein the aromatic core is a benzene ring, having the general formula 1,

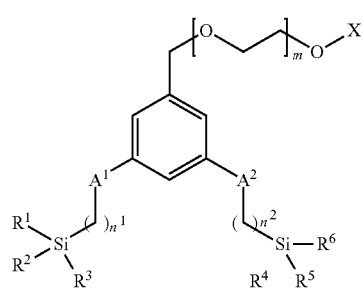

Formula 1 wherein

A$^1$ and A$^2$ are a covalent bond;

"n$^1$" is 2;

"n$^2$" is 2;

R$^1$ to R$^6$ are independently selected from a methoxy group and an ethoxy group;

"m" is an integer from 12 to 20; and

X is methyl.

6. A composition comprising a chemical compound according to claim 1 and a carrier.

7. A coated nanostructure comprising residues of the chemical compounds according to claim 1 or of a chemical compound comprising an aromatic core, or a carbocyclic, non-aromatic, core, and;

the core having covalently attached thereto:

at least two anchoring groups, each anchoring group comprising an activated silane group; and at least one hydrophilic group extending from the core, the hydrophilic group comprising one or more hydrophilic polymer residues with a molecular composition of (aO+bN)/(cC+dS+eSi+fP)>0.3 where a, b, c, d, e and f are the mol percentage of oxygen (O), nitrogen (N), carbon (C), sulfur (S), silicon (Si) and phosphorus (P), respectively;

wherein the number of hydrophilic groups extending from the core is from one to the number of ring structures in the core;

wherein one or both of the activated silanes in each of the chemical compounds, has been covalently bonded to the surface of the nanostructure core.

8. The coated nanostructure according to claim 7, wherein the nanostructure comprises a polymeric framework comprising, or adorned with, at least five geminal bisphosphonate groups having the general formula —P=O(OR$^{11}$)(OR$^{12}$) wherein R$^{11}$ and R$^{12}$ are independently selected from a negative charge, H, an alkyl group and an aryl group, wherein the polymeric framework further comprises monomer residues containing a geminal bisphosphonate group and two organo-oxysilane groups.

9. The coated nanostructure according to claim 7, wherein the coated nanostructure has a hydrodynamic diameter of 4 to 8 nm.

10. The coated nanostructure according to claim 7, further comprising a manganese(II) or a gadolinium(III) ion.

11. The coated nanostructure according to claim 7, further comprising a radionuclide.

12. A method of magnetic resonance imaging (MRI), the method comprising administering a contrast agent to a subject, wherein the contrast agent comprises a composition comprising the coated nanostructure of claim 10.

13. A method of positron emission tomography (PET) imaging and/or single-photon emission computed tomography (SPECT) imaging or radiotherapy, the method comprising administering a contrast agent to a subject, wherein the contrast agent comprises a composition comprising the coated nanostructure of claim 11.

14. A composition comprising nanostructures according to claim 7 and a carrier.

15. A method for obtaining a coated nanostructure according to comprising the steps of
  providing a nanostructure core of a polymeric framework comprising geminal bisphosphonate groups; and
  contacting said nanostructure core with at least one of the chemical compounds according to claim 1 in a solvent.

16. The method according to claim 15, wherein the method is performed in the presence of urea at a concentration of 0.1-1 M.

\* \* \* \* \*